US011168351B2

(12) United States Patent
Hunsley et al.

(10) Patent No.: US 11,168,351 B2
(45) Date of Patent: Nov. 9, 2021

(54) STABILIZATION OF NUCLEIC ACIDS IN URINE

(71) Applicant: STRECK, INC., La Vista, NE (US)

(72) Inventors: Bradford A. Hunsley, Papillion, NE (US); Jianbing Qin, Omaha, NE (US)

(73) Assignee: STRECK, INC., La Vista, NE (US)

( * ) Notice: Subject to any disclaimer, the term of this patent is extended or adjusted under 35 U.S.C. 154(b) by 487 days.

(21) Appl. No.: 15/061,557

(22) Filed: Mar. 4, 2016

(65) Prior Publication Data
US 2016/0257995 A1 Sep. 8, 2016

Related U.S. Application Data

(60) Provisional application No. 62/128,774, filed on Mar. 5, 2015.

(51) Int. Cl.
*C12Q 1/68* (2018.01)
*C12Q 1/6806* (2018.01)

(52) U.S. Cl.
CPC .................. *C12Q 1/6806* (2013.01)

(58) Field of Classification Search
CPC ............ C12Q 1/6806; C12Q 2527/101; C12Q 2527/125; C12Q 2527/137
USPC ......................................... 435/6.1
See application file for complete search history.

(56) References Cited

U.S. PATENT DOCUMENTS

| | | |
|---|---|---|
| 1,432,249 A | 10/1922 | Robert |
| 1,922,799 A | 8/1933 | Gaus |
| 2,250,666 A | 7/1941 | Webb |
| 2,690,624 A | 10/1954 | Phillips |
| 2,930,570 A | 3/1960 | Leedy |
| 3,781,120 A | 12/1973 | Engelhardt |
| 3,867,521 A | 2/1975 | Miskel et al. |
| 3,872,730 A | 3/1975 | Ringrose et al. |
| 3,874,384 A | 4/1975 | Deindoerfer et al. |
| 3,879,295 A | 4/1975 | Glover et al. |
| 3,973,913 A | 8/1976 | Louderback |
| 3,994,085 A | 11/1976 | Groselak et al. |
| 4,043,453 A | 8/1977 | Greenlee |
| 4,318,090 A | 3/1982 | Narlow et al. |
| 4,436,821 A | 3/1984 | Ryan |
| 4,513,522 A | 4/1985 | Selenke |
| 4,515,890 A | 5/1985 | Manderino et al. |
| 4,579,759 A | 4/1986 | Breuers |
| 4,584,219 A | 4/1986 | Baartmans |
| 4,675,159 A | 6/1987 | Al-Sioufi |
| 4,818,700 A | 4/1989 | Cregg et al. |
| 4,884,827 A | 12/1989 | Kelley |
| 4,921,277 A | 5/1990 | McDonough |
| 5,000,484 A | 3/1991 | Phelan et al. |
| 5,060,672 A | 10/1991 | Sandor et al. |
| 5,110,908 A | 5/1992 | Deich et al. |
| 5,135,125 A | 8/1992 | Andel et al. |
| 5,196,182 A | 3/1993 | Ryan |
| 5,213,765 A | 5/1993 | Kasai et al. |
| 5,250,438 A | 10/1993 | Ryan |
| 5,257,633 A | 11/1993 | Vogler et al. |
| 5,260,048 A | 11/1993 | Ryan |
| 5,270,208 A | 12/1993 | Ryan |
| 5,343,647 A | 9/1994 | Bulka |
| 5,366,249 A | 11/1994 | Diemert |
| 5,429,797 A | 7/1995 | Camiener |
| 5,447,842 A | 9/1995 | Simons |
| 5,457,024 A | 10/1995 | Goldbard |
| 5,459,073 A | 10/1995 | Ryan |
| 5,459,253 A | 10/1995 | Wolin et al. |
| 5,460,797 A | 10/1995 | Ryan |
| 5,468,022 A | 11/1995 | Linder et al. |
| 5,490,658 A | 2/1996 | Coward et al. |
| 5,501,954 A | 3/1996 | Mahr |
| 5,501,963 A | 3/1996 | Burckhardt |
| 5,512,343 A | 4/1996 | Shaw |
| 5,538,871 A | 7/1996 | Nuovo et al. |
| 5,540,358 A | 7/1996 | Wiles et al. |
| 5,560,657 A | 10/1996 | Morgan |
| 5,614,391 A | 3/1997 | Franciskvoich et al. |
| 5,618,664 A | 4/1997 | Kiessling |
| 5,629,147 A | 5/1997 | Asgari |
| D382,343 S | 8/1997 | Wandell et al. |
| 5,654,054 A | 8/1997 | Tropsha |

(Continued)

FOREIGN PATENT DOCUMENTS

| | | |
|---|---|---|
| AU | 2008288601 A1 | 4/2009 |
| CA | 2406463 | 1/2001 |

(Continued)

OTHER PUBLICATIONS

American Association for Cancer Research; 93rd Annual Meeting; Apr. 6-10, 2002; San Francisco, California; vol. 43, Mar. 2002.
Ashoor, G et al., "Trisomy 13 detection in the first trimester of pregnancy using a chromosome-selective cell-free DNA analysis method" Ultrasound in Obstetrics & Gynecology; 41(1):21-5, Nov. 23, 2012.
Barrett et al., "Implementing Prenatal Diagnosis Based on Cell-Free Fetal DNA: Accurate Identification of Factors Affecting Fetal DNA Yield," PLoS One, 6(10):e25202, Oct. 4, 2011.

(Continued)

*Primary Examiner* — Cynthia B Wilder

(74) *Attorney, Agent, or Firm* — Marshall, Gerstein & Borun LLP

(57) ABSTRACT

A composition and method for preserving a urine sample and a preservative delivery vessel are disclosed wherein treatment of the urine sample aids in preserving circulating cell-free nucleic acids in urine over a wide range of dilution ratios within temperature fluctuations that can occur during urine sample handling, storage and transportation. The urine sample preservation composition and method and preservative delivery vessel provide a method for obtaining high quality stabilized urinary cell-free nucleic acids for clinical diagnostics development and application.

29 Claims, 4 Drawing Sheets

(56) References Cited

U.S. PATENT DOCUMENTS

| | | |
|---|---|---|
| 5,688,516 A | 11/1997 | Raad et al. |
| 5,731,156 A | 3/1998 | Golbus |
| 5,741,638 A | 4/1998 | Yamane |
| 5,783,093 A | 7/1998 | Holme |
| 5,811,099 A | 9/1998 | Ryan |
| 5,817,519 A | 10/1998 | Zelmanovic et al. |
| 5,849,517 A | 12/1998 | Ryan |
| 5,858,699 A | 1/1999 | Granger et al. |
| 5,861,253 A | 1/1999 | Asgari et al. |
| 5,888,822 A | 3/1999 | Hengstenberg |
| 5,906,744 A | 5/1999 | Carroll et al. |
| 5,939,259 A | 8/1999 | Harvey et al. |
| 5,962,234 A | 10/1999 | Golbus |
| 5,976,014 A | 11/1999 | Petrick et al. |
| 5,977,153 A | 11/1999 | Camiener |
| 5,985,572 A | 11/1999 | Macfarlane |
| 6,013,240 A | 1/2000 | Behr et al. |
| 6,030,767 A | 2/2000 | Wagner |
| 6,043,032 A | 3/2000 | Yamagishi et al. |
| 6,072,086 A | 6/2000 | James et al. |
| 6,074,827 A | 6/2000 | Nelson |
| 6,077,235 A | 6/2000 | Serpentino et al. |
| 6,125,563 A | 10/2000 | Girerd |
| 6,128,840 A | 10/2000 | Biosvert |
| 6,168,922 B1 | 1/2001 | Harvey et al. |
| 6,177,163 B1 | 1/2001 | Block et al. |
| 6,190,609 B1 | 2/2001 | Chapman |
| 6,197,539 B1 | 3/2001 | Granger |
| 6,197,540 B1 | 3/2001 | Granger |
| 6,200,500 B1 | 3/2001 | Ryan |
| 6,210,889 B1 | 4/2001 | Drouin et al. |
| 6,218,531 B1 | 4/2001 | Ekenberg |
| 6,221,668 B1 | 4/2001 | Ryan et al. |
| 6,251,638 B1 | 6/2001 | Umansky et al. |
| 6,258,540 B1 | 7/2001 | Lo et al. |
| 6,287,820 B1 | 9/2001 | Umansky et al. |
| 6,337,189 B1 | 1/2002 | Ryan |
| 6,365,362 B1 | 4/2002 | Terstappen et al. |
| 6,399,388 B1 | 6/2002 | Ryan et al. |
| 6,403,377 B1 | 6/2002 | Ryan et al. |
| 6,406,915 B2 | 6/2002 | Ryan et al. |
| 6,527,242 B1 | 3/2003 | Kennedy |
| 6,527,957 B1 | 3/2003 | Deniega |
| 6,551,267 B1 | 4/2003 | Cohen et al. |
| 6,560,847 B2 | 5/2003 | Ohlsson |
| 6,579,672 B1 | 6/2003 | Granger |
| 6,581,973 B2 | 6/2003 | Levine et al. |
| 6,602,718 B1 | 8/2003 | Augello et al. |
| 6,617,170 B2 | 9/2003 | Augello et al. |
| 6,617,180 B1 | 9/2003 | Wang |
| 6,623,983 B1 | 9/2003 | Terstappen et al. |
| 6,630,301 B1 | 10/2003 | Gocke et al. |
| 6,645,731 B2 | 11/2003 | Terstappen et al. |
| 6,664,056 B2 | 12/2003 | Lo et al. |
| 6,759,217 B2 | 7/2004 | Kopreski et al. |
| 6,821,789 B2 | 11/2004 | Augello et al. |
| 6,860,513 B2 | 3/2005 | Kaufman |
| 6,884,573 B2 | 4/2005 | Fischer |
| 6,913,932 B2 | 7/2005 | Maples et al. |
| 6,916,634 B2 | 7/2005 | Kopreski |
| 6,939,671 B2 | 9/2005 | Kopreski |
| 6,994,790 B2 | 2/2006 | Corbin |
| 7,022,478 B2 | 4/2006 | Rainer et al. |
| 7,044,941 B2 | 5/2006 | Mathias |
| 7,208,275 B2 | 4/2007 | Gocke et al. |
| 7,267,980 B1 | 9/2007 | Mortari et al. |
| 7,282,371 B2 | 10/2007 | Helftenbein |
| 7,288,380 B1 | 10/2007 | Gocke et al. |
| 7,318,293 B2 | 1/2008 | Ardern |
| 7,332,277 B2 | 2/2008 | Dhallan |
| 7,332,288 B2 | 2/2008 | Terstappen et al. |
| 7,358,039 B2 | 4/2008 | Fischer |
| 7,390,663 B2 | 6/2008 | Ryan et al. |
| 7,398,999 B2 | 7/2008 | Kaufman |
| 7,419,832 B2 | 9/2008 | Hunsley |
| 7,442,506 B2 | 10/2008 | Dhallan |
| 7,445,901 B2 | 11/2008 | Kudlicki et al. |
| 7,478,513 B2 | 1/2009 | Baldwin |
| 7,569,350 B2 | 8/2009 | Gocke et al. |
| 7,651,838 B2 | 1/2010 | Paterlini-Brechot |
| 7,727,720 B2 | 6/2010 | Dhallan |
| 7,767,460 B2 | 8/2010 | Hunsley et al. |
| 8,304,187 B2 | 11/2012 | Fernando |
| 8,546,144 B2 | 10/2013 | Das et al. |
| 8,551,784 B2 | 10/2013 | Das et al. |
| 8,586,306 B2 | 11/2013 | Fernando |
| 8,841,077 B2 | 9/2014 | Paige et al. |
| 9,034,635 B2 | 5/2015 | Termaat et al. |
| 9,040,255 B2 | 5/2015 | Tsinberg |
| 9,120,849 B2 | 9/2015 | Chiklis et al. |
| 9,127,048 B2 | 9/2015 | Chiklis et al. |
| 9,657,227 B2 | 5/2017 | Fernando |
| 9,926,590 B2 | 3/2018 | Fernando |
| 9,926,950 B2 | 3/2018 | Ooki et al. |
| 9,956,281 B2 | 5/2018 | Ryan et al. |
| 10,006,861 B2 | 6/2018 | Kreifels et al. |
| 10,091,984 B2 | 10/2018 | Fernando et al. |
| 10,144,955 B2 | 12/2018 | Fernando |
| 10,294,513 B2 | 5/2019 | Fernando |
| 2001/0018192 A1 | 8/2001 | Terstappen et al. |
| 2001/0049895 A1 | 12/2001 | Burke |
| 2001/0051341 A1 | 12/2001 | Lo et al. |
| 2002/0045196 A1 | 4/2002 | Mahoney et al. |
| 2002/0066216 A1 | 6/2002 | DeLaCruz |
| 2002/0086346 A1 | 7/2002 | Ryan |
| 2002/0119503 A1 | 8/2002 | Ryan et al. |
| 2003/0113705 A1 | 6/2003 | McMillian |
| 2003/0232377 A1 | 12/2003 | Thomas |
| 2004/0014107 A1 | 1/2004 | Garcia-Blanco et al. |
| 2004/0038424 A1 | 2/2004 | Maples |
| 2004/0137417 A1 | 7/2004 | Ryan |
| 2005/0029559 A9 | 2/2005 | Ahn et al. |
| 2005/0049793 A1 | 3/2005 | Paterlini-Brechot |
| 2005/0232377 A1 | 3/2005 | Paterlini-Brechot |
| 2005/0107316 A1 | 5/2005 | Strebhardt et al. |
| 2005/0164241 A1 | 7/2005 | Hahn et al. |
| 2005/0181353 A1 | 8/2005 | Rao et al. |
| 2005/0181463 A1 | 8/2005 | Rao et al. |
| 2005/0277204 A1 | 12/2005 | Hollis et al. |
| 2006/0008807 A1 | 1/2006 | O'Hara et al. |
| 2006/0105372 A1 | 5/2006 | Bair et al. |
| 2006/0194192 A1 | 8/2006 | Rao et al. |
| 2006/0210429 A1 | 9/2006 | Hunsley et al. |
| 2007/0111233 A1 | 5/2007 | Bianchi et al. |
| 2007/0134658 A1 | 6/2007 | Bohmer |
| 2007/0178478 A1 | 8/2007 | Dhallan |
| 2007/0202525 A1 | 8/2007 | Quake et al. |
| 2007/0243548 A1 | 10/2007 | Bischoff |
| 2007/0243549 A1 | 10/2007 | Bischoff |
| 2007/0251337 A1 | 11/2007 | Reed et al. |
| 2007/0298406 A1 | 12/2007 | Martorell et al. |
| 2008/0020390 A1 | 1/2008 | Mitchell et al. |
| 2008/0057502 A1 | 3/2008 | Kopreski |
| 2008/0081689 A1 | 4/2008 | Seelig et al. |
| 2008/0096217 A1 | 4/2008 | Kopreski |
| 2008/0102470 A1 | 5/2008 | Dawson |
| 2008/0108071 A1 | 5/2008 | Thompson |
| 2008/0119645 A1 | 5/2008 | Griffey et al. |
| 2008/0206866 A1 | 8/2008 | Zieglschmid et al. |
| 2008/0261292 A1 | 10/2008 | Kopreski |
| 2008/0318801 A1 | 12/2008 | Leung et al. |
| 2009/0034446 A1 | 2/2009 | Adams et al. |
| 2009/0081678 A1 | 3/2009 | Ryan et al. |
| 2009/0215036 A1 | 8/2009 | Stropp et al. |
| 2009/0308303 A1 | 12/2009 | Burlando |
| 2010/0167271 A1 | 7/2010 | Ryan |
| 2010/0184069 A1 | 7/2010 | Fernando et al. |
| 2010/0190796 A1 | 7/2010 | Verkman et al. |
| 2010/0209930 A1 | 8/2010 | Fernando |
| 2010/0216153 A1 | 8/2010 | Lapidus et al. |
| 2010/0317107 A1 | 12/2010 | Ryan |
| 2011/0027771 A1 | 2/2011 | Deng |
| 2011/0053208 A1 | 3/2011 | Reiss |
| 2011/0110975 A1 | 5/2011 | Grunkemeyer et al. |

(56) References Cited

U.S. PATENT DOCUMENTS

| | | |
|---|---|---|
| 2011/0111410 A1 | 5/2011 | Ryan et al. |
| 2012/0164676 A1 | 6/2012 | Tsinberg |
| 2012/0308990 A1 | 12/2012 | TerMaat |
| 2013/0034860 A1 | 2/2013 | Fernando |
| 2013/0209985 A1 | 8/2013 | Dudaronek et al. |
| 2014/0054508 A1 | 2/2014 | Fernando |
| 2014/0080112 A1 | 3/2014 | Ryan |
| 2014/0199681 A1 | 7/2014 | Ryan |
| 2014/0274740 A1 | 9/2014 | Srinivasan et al. |
| 2015/0030578 A1 | 1/2015 | Releford et al. |
| 2015/0301037 A1 | 10/2015 | Tsinberg et al. |
| 2016/0143268 A1 | 5/2016 | Ryan |
| 2016/0174544 A1 | 6/2016 | Fernando et al. |
| 2017/0052173 A1 | 2/2017 | Hunsley et al. |
| 2017/0097361 A1 | 4/2017 | Alt et al. |
| 2017/0145475 A1 | 5/2017 | Hunsley et al. |
| 2018/0243406 A1 | 8/2018 | Ryan et al. |
| 2019/0127780 A1 | 5/2019 | Hunsley et al. |
| 2019/0177774 A1 | 6/2019 | Connelly et al. |

FOREIGN PATENT DOCUMENTS

| | | |
|---|---|---|
| CN | 104634628 A | 5/2015 |
| CN | 107525818 A | 12/2017 |
| DE | 19928820 | 12/2000 |
| EP | 1031626 A1 | 8/2000 |
| EP | 1207208 A2 | 5/2002 |
| EP | 1217372 A1 | 6/2002 |
| EP | 1212613 B1 | 5/2007 |
| EP | 1816461 A1 | 8/2007 |
| EP | 1889921 A2 | 2/2008 |
| EP | 1425294 B1 | 7/2008 |
| EP | 2228453 A1 | 9/2010 |
| EP | 2216416 | 11/2010 |
| EP | 2411808 B1 | 2/2012 |
| EP | 2674502 A1 | 12/2013 |
| EP | 2704740 A2 | 3/2014 |
| EP | 2814981 A2 | 12/2014 |
| EP | 3118623 A1 | 1/2017 |
| EP | 3225699 A1 | 10/2017 |
| EP | 3572531 A1 | 11/2019 |
| JP | 4453999 B2 | 4/2010 |
| WO | 1990/10715 A1 | 9/1990 |
| WO | 93/05650 | 4/1993 |
| WO | 94/02646 | 2/1994 |
| WO | 95/26417 A1 | 10/1995 |
| WO | 1997/45729 A1 | 12/1997 |
| WO | 98/02528 A1 | 1/1998 |
| WO | 98/02740 A1 | 1/1998 |
| WO | 1998/44158 A1 | 10/1998 |
| WO | 98/59042 A1 | 12/1998 |
| WO | 2000/00813 A1 | 1/2000 |
| WO | 00/06780 A1 | 2/2000 |
| WO | 00/75647 A1 | 12/2000 |
| WO | 00/77235 | 12/2000 |
| WO | WO-01/014872 A1 | 3/2001 |
| WO | 01/79851 A1 | 10/2001 |
| WO | 01/98542 | 12/2001 |
| WO | 02/055985 | 7/2002 |
| WO | 2002/56030 A2 | 7/2002 |
| WO | 03/018757 A2 | 3/2003 |
| WO | 2003/35895 A2 | 5/2003 |
| WO | 03/019141 A2 | 6/2003 |
| WO | 03/069344 | 8/2003 |
| WO | 2003/074723 A2 | 9/2003 |
| WO | 2003/74730 A1 | 9/2003 |
| WO | 03/095974 | 11/2003 |
| WO | 2006/100063 A2 | 9/2006 |
| WO | 2007/022483 A2 | 2/2007 |
| WO | 2008/107724 A2 | 9/2008 |
| WO | 2008/111981 A1 | 9/2008 |
| WO | WO-2009/105499 A1 | 8/2009 |
| WO | WO-2010/078194 A1 | 7/2010 |
| WO | 2010/096323 A1 | 8/2010 |
| WO | 2010/123908 A1 | 10/2010 |
| WO | WO-2010/132756 A2 | 11/2010 |
| WO | 2011/014741 A1 | 2/2011 |
| WO | 2011/057184 | 5/2011 |
| WO | 2011/082415 A2 | 7/2011 |
| WO | 2012/145662 A1 | 10/2012 |
| WO | WO-2012/151391 A2 | 11/2012 |
| WO | 2012/166913 A1 | 12/2012 |
| WO | WO-2012/166913 A1 | 12/2012 |
| WO | WO-2013/019290 A2 | 2/2013 |
| WO | 2013/086428 A1 | 6/2013 |
| WO | 2013/123030 A3 | 8/2013 |
| WO | 2014/029791 A1 | 2/2014 |
| WO | 2014/049022 A1 | 4/2014 |
| WO | WO-2015/134053 A1 | 9/2015 |
| WO | 2017/031354 A2 | 2/2017 |
| WO | WO-2017/201612 A1 | 11/2017 |
| WO | WO-2017/218789 A1 | 12/2017 |
| WO | WO-2018/022991 A1 | 2/2018 |
| WO | WO-2018/031903 A1 | 2/2018 |
| WO | WO-2018/035340 A1 | 2/2018 |
| WO | WO-2019/079743 A1 | 4/2019 |
| WO | WO-2019/090126 A1 | 5/2019 |
| WO | WO-2020/140035 A1 | 7/2020 |

OTHER PUBLICATIONS

Bayindir, B et al., "Noninvasive Prenatal Testing Using a Novel Analysis Pipeline to Screen for All Autosomal Fetal Aneuploidies Improves Pregnancy Management," European Journal of Human Genetics. Jan. 14, 2015.

Beck, J et al., Digital Droplet PCR for Rapid Quantification of Donor DNA in the Circulation of Transplant Recipients as a Potential Universal Biomarker of Graft Injury. Clinical chemistry; 59(12):1732-41, Dec. 1, 2013.

Benachi, A et al., Cell-Free DNA Analysis in Maternal Plasma in Cases of Fetal Abnormalities Detected on Ultrasound Examination. Obstetrics &. Gynecology; 125(6):1330-7, Jun. 1, 2015.

Bethel, K et al., "Fluid phase biopsy for detection and characterization of circulating endothelial cells in myocardial infarction," Physical biology; 11(1):016002, Feb. 1, 2014.

Bevilacqua, E et al., "Performance of screening for aneuploidies by cell-free DNA analysis of maternal blood in twin pregnancies," Ultrasound in Obstetrics & Gynecology; 45(1):61-6, Jan. 1, 2015.

Bianchi et al., "PCR Quantification of Fetal Cells in Maternal Blood in Normal and Aneuploid Pregnancies" Am J. Hum. Genet. 61:822-829, 1997.

Bianchi, "Invited Editorial Fetal DNA in Maternal Plasma: The Plot Thickens and the Placental Barrier Thins," The American Society of Human Genetics, 62:763-764, 1998.

Bianchi, D et al., "Fetal sex chromosome testing by maternal plasma DNA sequencing: clinical laboratory experience and biology," Obstetrics & Gynecology; 125(2):375-82, Feb. 1, 2015.

Bianchi, DW et al., "DNA sequencing versus standard prenatal aneuploidy screening" New England Journal of Medicine;370(9):799-808, Feb. 27, 2014.

Bina-Stein, et al., Aurintricarboxylic Acid is a Nonspecific Enzyme Inhibitor, Department of Chemistry, Yale University, New Haven, Connecticut. 1975, 12:191-193.

Biocept—Expands Patent Protection for Liquid Biopsy Platform dated Jun. 1, 2015; http://ir.biocept.com/releasedetail.cfm?releaseID= 915635.

Biocept (BIOC) Announces Patent for Blood Collection and Transport Tube; StreetInsider.com; http://www.streetinsider.com/corporate+news/biocept+(BIOC)+Announces; Jun. 1, 2015.

Bioreceptor Ferro fluids: Novel Characteristics and their Utility in Medical Applications; P. A. Liberti, J. N. Chiarappa, A. C. Hovespian, C. G. Rao; Supplied by the British Library; 1996 Kluwer Academic Publishers.

Botezatu et al. "Genetic Analysis of DNA Excreted in Urine: A New Approach for Detecting Specific Genomic DNA Sequences from Cells Dying in an Organism" Clinical Chemistry 46:8, 1078-1084 (2000).

(56) References Cited

OTHER PUBLICATIONS

Brar, H et al., "The fetal fraction of cell-free DNA in maternal plasma is not affected by a priori risk of fetal trisomy," The Journal of Maternal-Fetal & Neonatal Medicine; 26(2):143-5, Jan. 1, 2013.
Bruno, D et al., Use of copy number deletion polymorphisms to assess DNA chimerism. Clinical chemistry; 60(8)1105-14, Aug. 1, 2014.
Buysse, K et al. "Reliable noninvasive prenatal testing by massively parallel sequencing of circulating cell-free DNA from maternal plasma processed up to 24h after venipuncture," Clinical biochemistry; 46(18):1783-6 Dec. 31, 2013.
Carlsson, A et al., "Circulating Tumor Microemboli Diagnostics for Patients with Non-Small-Cell Lung Cancer," Journal of Thoracic Oncology; 9(8).1111-9, Aug. 1, 2014.
Chan et al, "Hypermethylated RASSFIA in maternal Plasma: A Universal Fetal DNA Marker that Improves the Reliability of Noninvasive Prenatal Diagnosis," Clinical Chemistry, 2211-2218, 52(12), 2006.
Chinnapapagari et al., "Treatment of Maternal Blood Samples with Formaldehyde does not alter the Proportion of Circulatory Fetal Nucleic Acids (DNA and mRNA) in Maternal Plasma", Technical Briefs, University Women's Hospital/Dept. of Research, Basel, Switzerland, pp. 652-655, Apr. 2005.
Chiu, Rosa et al.,"Effects of Blood-Processing Protocols on Fetal and Total DNA Quantification in Maternal Plasma," Clinical Chemistry 47:9, 1607-1613, 2001.
Chudziak, J et al., "Clinical evaluation of a novel microfluidic device for epitope-independent enrichment of circulating tumour cells in patients with small cell lung cancer," The Analyst;141(2):669-78, Nov. 2015.
Chung et al., "Lack of Dramatic Enrichment of Fetal DNA in Maternal Plasma by Formaldehyde Treatment," Clinical Chemistry, 51, No. 3, 2005.
Chung et al.; "Detrimental Effect of Formaldehyde on Plasma RNA Detection" 51 (6): 10, Jul. 12, 2010.
Clark-Ganheart et al., "Use of Cell-Free DNA in the Investigation of Intrauterine Fetal Demise and Miscarriage," Obstetrics & Gynecology; 125(6):1321-9, Jun. 1, 2015.
Clinical Applications of Flow Cytometry: Immunophenotyping of Leukemic Cells; Approved Guideline; Jun. 1998; vol. 18 No. 8; NCCLS.
Comas, C et al., "Initial Experience with Non-Invasive Prenatal Testing of Cell-Free DNA for Major Chromosomal Anomalies in a Clinical Setting," The Journal of Maternal-Fetal & Neonatal Medicine; (0):1-6, Aug. 12, 2014.
Costa et al. "Fetal Expressed Gene Analysis in maternal Blood: A New Tool for Noninvasive Study of the Fetus" Clinical Chemistry, vol. 49, No. 6, pp. 981-983, 2003.
Curnow et al., "Detection of Triploid, Molar, and Vanishing Twin Pregnancies by a Single-Nucleotide Polymorphism-Based Noninvasive Prenatal Test," American Journal of Obstetrics and Gynecology; 212(1):79-e1 Jan. 2015.
Dash et al. "Using Noninvasive Prenatal Testing for Aneuploidies in a Developing Country: Lessons Learnt" Journal of Fetal Medicine, 1(3):131-5, 2014.
Decision to Refuse a European Patent Application dated May 3, 2007, Application No. 03 256 535.0-2113.
Denis et al. "Efficient Detection of BRAF Mutation in Plasma of Patients after Long-term Storage of Blood in Cell-Free DNA Blood Collection Tubes" Clinical Chemistry, 61(6):886-8, Jun. 1, 2015.
Dhallan et al., "Methods to Increase the Percentage of Free Fetal DNA Recovered from the Maternal Circulation," JAMA vol. 291, No. 9, 1114-1119, Mar. 3, 2004.
Dharajiya et al. "Noninvasive Prenatal Testing Using Cell-Free Fetal DNA in Maternal Plasma" Current Protocols in Human Genetics, 8-15, Jan. 20, 2015.
Diamond et al. "Diverse and Targetable Kinase Alterations Drive Histiocytic Neoplasms" Cancer discovery: CD-15, Nov. 15, 2015.

Ding, et al., MS Analysis of Single-Nucleotide Differences in Circulating Nucleic Acids: Application to Noninvasive Prenatal Diagnosis, 101:10762-10767, 2004.
Fairbrother et al. "Clinical experience of noninvasive prenatal testing with cell-free DNA for fetal trisomies 21, 18, and 13, in a general screening population" Prenatal Diagnosis; 33(6):580-3, Jun. 1, 2013.
Fernando et al., "Stabilization of cell-free RNA in blood samples using a new collection device" Clinical Biochemistry, vol. 45, No. 16-17, pp. 1497-1502, dated Nov. 1, 2012.
Fernando et al., "Stabilization of Cell-Free RNA in Plasma for Noninvasive Diagnosis and Prognosis" URL:http://www.streck.com/resources/Cell_Stabilization/02_Paper_Cell-Free_RNA_BCT_Stabilization_of_Cell-Free_RNA_in_Plasma.pdf Retrieved on May 15, 2014.
Futch et al. "Initial clinical laboratory experience in noninvasive prenatal testing for fetal aneuploidy from maternal plasma DNA samples" Prenatal Diagnosis; 33(6):569-74, Jun. 1, 2013.
Gielis, E.M., "Cell-Free DNA: An Upcoming Biomarker in Transplantation," American Journal of Transplantation May 13, 2015.
Gil et al. "Cell-free DNA analysis for trisomy risk assessment in first-trimester twin pregnancies" Fetal Diagnosis and Therapy; 35(3):204-11, Nov. 15, 2013.
Gil et al. "Implementation of maternal blood cell-free DNA testing in early screening for aneuploidies" Ultrasound in Obstetrics & Gynecology; 42(1):34-40, Jun. 7, 2013.
Gil et al. "UK NHS pilot study on cell-free DNA testing in screening for fetal trisomies: factors affecting uptake" Ultrasound in Obstetrics & Gynecology; 45(1):67-73. Jan. 1, 2015.
Gonzalez, et al., "Application of Fetal DNA Detection in Maternal Plasma: A Prenatal Diagnosis Unit Experience," Journal of Histochemistry & Cytochemistry, 53(3): 307-314, 2005.
Grömminger et al. "Fetal aneuploidy detection by cell-free DNA sequencing for multiple pregnancies and quality issues with vanishing twins" Journal of Clinical Medicine; 3(3):679-92, Jun. 25, 2014.
Gross et al. "Rapid changes in circulating tumor cells following anti-angiogenic therapy" Convergent Science Physical Oncology; 1(1):015002, Sep. 15, 2015.
Haaland, Arne. *Molecules and models: the molecular structures of main group element compounds.* Oxford University Press, 2008. (abstract available at http://www.oxfordscholarship.com/view/10.1093/acprof.oso/9780199235353.001.0001/acprof-9780199235353-chapter-12).
Hidestrand et al. "Influence of temperature during transportation on cell-free DNA analysis" Fetal diagnosis and Therapy; 31(2):122-8, 2012.
Hindson et al. "High-throughput droplet digital PCR system for absolute quantitation of DNA copy number" Analytical Chemistry; 83(22):8604-10, Oct. 28, 2011.
Holford et al, Stability of beta-actin mRNA in plasma, Annals of the New York Academy of Science, Aug. 2008, 108-111, 1137.
Holmberg et al. "Akonni TruTip® and Qiagen® methods for extraction of fetal circulating DNA—evaluation by real-time and digital PCR" PloS One; 8(8):e73068, Aug. 2013.
Hooks et al. "Non-invasive risk assessment of fetal sex chromosome aneuploidy through directed analysis and incorporation of fetal fraction" Prenatal Diagnosis; 34(5):496-9, May 2014.
http://ir.biocept.com/secfiling.cfm?filingid=1193125-15-16425&cik=1044378; Biocept Completing the Answer; Jan. 21, 2015.
Hynek et al., "MoM-based Approach to Noninvasive Prenatal Testing Using Exponentially Weighted Moving Average Chart and Chromosomal Fingerprint" International Journal of Biomedicine and Healthcare: 12, 2015.
Ignatiadis et al. "Circulating Tumor Cells and Circulating Tumor DNA: Challenges and Opportunities on the Path to Clinical Utility" Clinical Cancer Research; 21 (21): 4786-800, Nov. 2015.
Jensen et al. "High-throughput massively parallel sequencing for fetal aneuploidy detection from maternal plasma" PloS One; 8(3): e57381, Mar. 2013.
Jeon et al. "The feasibility study of non-invasive fetal trisomy 18 and 21 detection with semiconductor sequencing platform" PLoS One; 9(10):e110240, Oct. 20, 2014.

(56) References Cited

OTHER PUBLICATIONS

Juneau et al. "Microarray-based cell-free DNA analysis improves noninvasive prenatal testing" Fetal Diagnosis and Therapy; 36(4):282-6, 2014.
Kadam et al. "Quantitative measurement of cell-free plasma DNA and applications for detecting tumor genetic variation and promoter methylation in a clinical setting" The Journal of Molecular Diagnostics. Jul. 31, 2012;14(4):346-56.
Kagan et al "A Sample Preparation and Analysis System for Indentification of Circulating Tumor Cells"; vol. 25, No. 1; Spring 2002; Journal of Clinical Ligand Assay.
Kashiwasaki et al. "Influence of upper and lower thermoneitral room temperatures (20° C. and 25° C.) on fasting and post-prandial resting metabolism under different outdoor temperatures," European Journal of Clinical Nutrition, vol. 44, pp. 405-413, 1990.
Katz et al. No Date. "Mass-Volume Equivalents of Common Chemical Solids." Available at <http://www.chymist.com/Mass-volume%20equivalents.pdf>. Accessed Oct. 22, 2015. 4 pages.
Kelly, Brian N., "Circulating microRNA as a biomarker of human growth hormone administration to patients," Mar. 12, 2013, vol. 6, Issue 3.
Kidess et al. "Mutation profiling of tumor DNA from plasma and tumor tissue of colorectal cancer patients with a novel, high-sensitivity multiplexed mutation detection platform" Oncotarget. Feb. 2015; 6(4):2549.
Kirkizlar et al. "Detection of Clonal and Subclonal Copy-Number Variants in Cell-Free DNA from Patients with Breast Cancer Using a Massively Multiplexed PCR Methodology" Translational oncology. Oct. 31, 2015;8(5):407-16.
Kreuzer et al. "Highly Sensitive and specific Fluorescence Reverse Transcription-PCR Assay for the Psuedogene-free Detection of β-actin Transcripts as Quantitative Reference" Clinical Chemistry, vol. 45, No. 2, pp. 297-300, 1999.
Kwee et al. "Measurement of Circulating Cell-Free DNA in Relation to 18F-Fluorocholine PET/CT Imaging in Chemotherapy-Treated Advanced Prostate Cancer" Clinical and Translational Science. Feb. 1, 2012;5(1):65-70.
Lambert-Messerlian et al. "Feasibility of using plasma rather than serum in first and second trimester multiple marker Down's syndrome screening. Journal of medical screening" Dec. 1, 2012;19(4):164-70.
Lanman et al.. "Analytical and clinical validation of a digital sequencing panel for quantitative, highly accurate evaluation of cell-free circulating tumor DNA" PloS one. Oct. 16, 2015;10(10):e0140712.
Lee et al. "Performance of Momguard, a new non-invasive prenatal testing protocol developed in Korea" Obstetrics & Gynecology Science. Sep. 1, 2015;58(5):340-5.
Lee et al., "Survival of Donor Leukocyte Subpopulations in Immunocompetent Transfusion Recipients: Frequent Long-Term Microchimerism in Severe Trauma Patients," Blood, 3127-3139, 93, 1999.
Lee, Thomas "Down Syndrome and Cell-Free Fetal DNA in Archived Maternal Serum" (AM J. Obstet Gynecol 2002; 187: 1217-21).
Li, et al., "Detection of Paternally Inherited Fetal Point Mutations for β-Thalassemia Using Size-Fractionated Cell-Free DNA in Maternal Plasma," available at: www.jama.com, 293:843-849, 2005.
Liao et al. "Noninvasive prenatal diagnosis of common aneuploidies by semiconductor sequencing" Proceedings of the National Academy of Sciences. May 20, 2014;111(20):7415-20.
Liu et al. "Placental mosaicism for Trisomy 13: a challenge in providing the cell-free fetal DNA testing" Journal of assisted reproduction and genetics. May 1, 2014;31(5).589-94.
Lo et al. "Fetal Cell-Free Plasma DNA Concentrations in Maternal Blood are Stable 24 hours after" Clinical-Chemistry (Jan. 19, 2012).
Lo et al. "Presence of Fetal DNA in Maternal Plasma and Serum" The Lancet, 350, 485-87, 1997.
Lo et al., "Noninvasive prenatal diagnosis for fetal chromosomal aneuploidies by maternal plasma nucleic acid analysis" Clinical Chemistry, American Association for Clinical Chemistry, Washington DC Lnkd—Doi:10.1373/Clinchem.2007.100016, vol. 54, No. 3, pp. 461-466, Jan. 17, 2008.
Lo, "Fetal DNA in Maternal Plasma: Biology and Diagnostic Applications," Clinical Chemistry 46:12 1903-1906, 2000.
Lo, et al., "Increased Fetal DNA Concentrations in the Plasma of Pregnant Women Carrying Fetuses with Trisomy 21" Clinical Chemistry 45:10, 1747-1751 (1999).
Lo, et al., "Quantitative Analysis of Fetal DNA in Maternal Plasma and Serum: Implications for Noninvasive Prenatal Diagnosis," by The American Society of Human Genetics, 62:768-775, 1998.
Lo, Y M Dennis "Circulating Nucleic Acids in Plasma and Serum: An Overview", Annals of the New York Academy of Sciences vol. 945, Issue pp. 1-291 (Sep. 2001).
Lo, Y M Dennis "Molecular Testing of Urine: Catching DNA on the way out" Clinical Chemistry 46, No. 8, 2000.
Lo, Y M Dennis, "Fetal Nucleic Acids in Maternal Plasma, Toward the Development of Noninvasive Prenatal Diagnosis of Fetal Chromosomal Aneuploidies," New York Academy of Sciences, 2008.
Lu et al. Detection and Characterization of Circulating Tumour Cells from Frozen Peripheral Blood Mononuclear Cells. Journal of Circulating Biomarkers. Dec. 1, 2015;35(12):1243-6.
Machaca et al., "Characterization of apoptosis-like endonuclease activity in avian thymocytes," Biology of the Cell, 15-22, 76(1), Elsevier, Paris France, Jan. 1, 1992.
Madabusi et al., "RNA extraction for Arrays," Methods in Enzymology, 1-14, 411, 2006.
McCullough et al. "Non-invasive prenatal chromosomal aneuploidy testing-clinical experience: 100,000 clinical samples" PLoS One. Oct. 7, 2014;9(10):e109173.
Nair et al. "An observational study of circulating tumor cells and (18) F-FDG PET uptake in patients with treatment-naive non-small cell lung cancer" PloS One. Jul. 5, 2013;8(7):e67733.
Nicolaides et al. "Validation of targeted sequencing of single-nucleotide polymorphisms for non-invasive prenatal detection of aneuploidy of chromosomes 13, 18, 21; X, and Y" Prenatal Diagnosis. Jun. 1, 2013;33(6):575-9.
Norton et al. "Cell-free DNA analysis for noninvasive examination of trisomy" New England Journal of Medicine. Apr. 23, 2015;372(17):1589-97.
Norton et al. "Non-Invasive Chromosomal Evaluation (NICE) Study: results of a multicenter prospective cohort study for detection of fetal trisomy 21 and trisomy 18" American Journal of Obstetrics and Gynecology. Aug. 31, 2012;207(2): 137-01.
Ono et al. "Circulating microRNA Biomarkers as Liquid Biopsy for Cancer Patients: Pros and Cons of Current Assays" Journal of clinical medicine. Oct. 23, 2015;4(10):1890-907.
Palmer et al., "Flow cytometric determination of residual white blood cell levels in preserved samples from leukoreduced blood products," Transfusion, 118-128, 48(1), Jan. 2008.
Pan, et al., "Cell-free Fetal DNA Levels in Pregnancies Conceived by IVF", Human Reproduction, 20(11):3152-3156, 2005.
Persico et al. "Cell-free DNA testing in the maternal blood in high-risk pregnancies after first trimester combined screening" Prenatal Diagnosis. Jan. 1, 2016.
Pertl, et al., "Fetal DNA in Maternal Plasma: Emerging Clinical Applications," by The American College of Obstetricians and Gynecologists, 98:483-490, 2001.
Pinzani et al., "Circulating Nucleic Acids in Cancer and Pregnancy," Methods: A Companion to Methods in Enzymology, 302-307, 40 (4), Academic Press Inc., New York, Apr. 1, 2010.
Punnoose et al. "PTEN loss in circulating tumour cells correlates with PTEN loss in fresh tumour tissue from castration-resistant prostate cancer patients" British Journal of Cancer. Oct. 20, 2015;113(8):1225-33.
Puren et al., Laboratory operations, specimen processing, and handling for viral load testing and surveillance, Journal of Infectious Diseases, S27-S36, 201(supp 1), University of Chicago Press, Chicago Il, Apr. 15, 2010.
Quezada et al, "Fetal fraction of cell-free DNA in maternal plasma in the prediction of spontaneous preterm delivery." Ultrasound in Obstetrics & Gynecology. Jan. 1, 2015;45(1):101-5.

(56) References Cited

OTHER PUBLICATIONS

Quezada et al, "Screening for trisomies 21, 18 and 13 by cell-free DNA analysis of maternal blood at 10-11 weeks' gestation and the combined test at 11-13 weeks" Ultrasound in Obstetrics & Gynecology. Jan. 1, 2015;45(1):36-41.
Rait et al. "Conversions of formaldehyde-modified 2'-deoxyadenosine 5'-monophosphate in conditions modeling formalin-fixed tissue dehydration" J. Histochem Cytochem 54(3): 301-10 (Mar. 1, 2006).
Risberg B. "Establishment of PCR based methods for detection of ctDNA in blood." Thesis submitted for the Master's degree in Biomedicine. Oslo University Hospital, Institute for Cancer Research, Department of Genetics and Oslo and Akershus University College of Applied Sciences. May 5, 2013.
Ruiz et al. "Limited genomic heterogeneity of circulating melanoma cells in advanced stage patients" Physical Biology. Feb. 1, 2015;1. 2(1):016008.
Salvianti et al. "Single circulating; tumor cell sequencing as an advanced tool in cancer management" Expert review of molecular diagnostics. Nov. 27, 2015:1-3.
Samango-Sprouse et al. "SNP-based non-invasive prenatal testing detects sex chromosome aneuploidies with high accuracy" Prenatal diagnosis. Jul. 1, 2013;33(7):643-9.
Samoila et al. "Method development and validation for clinical cfDNA extraction from blood" InASCO Annual Meeting Proceedings May 20, 2015 (vol. 33, No. 15_suppl, p. e22185).
Samuel et al. "The effect of chorionic villus sampling on the fraction of cell-free fetal DNA in maternal plasma" The Journal of Maternal-Fetal & Neonatal Medicine. Oct. 15, 2015:1-4.
Schatz et al.; "Preservation of Cell-Free DNA in Stored Blood Samples for the Analysis of the (M) Sept9 Colorectal Cancer Screening Marker Enables Sample Shipment by Mail", May 2011, Published as a poser at the conference on International federation of clinical chemistry and laboratory medicine Worldlab and EU, Berlin, Germany.
Scheffer et al. "Noninvasive fetal blood group genotyping of rhesus D, c, E and of K in alloimmunised pregnant women: evaluation of a 7-year clinical experience" BJOG: An International Journal of Obstetrics & Gynaecology. Oct. 1, 2011;118(11):1340-8.
Schiavon et al. "Analysis of ESR1 mutation in circulating tumor DNA demonstrates evolution during therapy for metastatic breast cancer" Science translational medicine. Nov. 11, 2015;7(313):313ra182-.
Sekizawa et al.; "Apoptosis in Fetal Nucleated Erythrocytes Circulating in Maternal Blood" Prenatal Diagnosis; 20: 886-889, 2000.
Seo et al, "An Experience of Using the Harmony Test for Genomics-Based Non-Invasive Prenatal Testing" Journal of Laboratory Medicine and Quality Assurance. Mar. 1, 2015;37(1):44-6.
Shi et al. "Feasibility of noninvasive prenatal testing for common fetal aneuploidies in an early gestational window" Clinica Chimica. Acta. Jan. 15, 2015;439:24-8.
Sigma-Aldrich. "1-Aza-3,7-dioxabicyclo[3.3.0]octane-5-methanol solution." Available online at www.sigmaaldrich.com/catalog/product/aldrich/417807?lang=en&region=US. 5 pages. Accessed Jan. 13, 2014.
Sillence et al. "Fetal Sex and RHD Genotyping, with Digital PCR Demonstrates Greater Sensitivity than Real-time PCR" Clinical Chemistry. Nov. 1, 2015;61(11):1399-407.
Smid et al., "Evaluation of Different Approaches for Fetal DNA Analysis from Maternal Plasma and Nucleated Blood Cells", Technical Briefs, pp. 1570-1572, 1999.
Smid et al., "Quantitative Analysis of Fetal DNA in Maternal Plasma in Pathological Conditions Associated with Placental Abnormalities," Annals New York Academy of Sciences, 951:133-137, 2001.
Song et al. "Non-invasive prenatal testing for fetal aneuploidies in the first trimester of pregnancy" Ultrasound in Obstetrics & Gynecology, Jan. 1, 2015;45(1):55-60.
Sparks et al. "Noninvasive prenatal detection and selective analysis of cell-free DNA obtained from maternal blood: evaluation for trisomy 21 and trisomy 18" American Journal of Obstetrics and Gynecology, Apr. 30, 2012;206(4):319-e1.
Sparks et al. "Selective analysis of cell-free DNA in maternal blood for evaluation of fetal trisomy" Prenatal Diagnosis. Jan. 1, 2012;32(1):3-9.
Stokowski et al. "Clinical performance of non-invasive prenatal testing (NIPT) using targeted cell-free DNA analysis in maternal plasma with microarrays or next generation sequencing (NGS) is consistent across multiple controlled clinical studies" Prenatal Diagnosis. Dec. 1, 2015;35(12):1243-6.
Stumm et al. "Diagnostic accuracy of random massively parallel sequencing for non-invasive prenatal detection of common autosomal aneuploidies: a collaborative study in Europe" Prenatal Diagnosis. Feb. 1, 2014;34(2):185-91.
Takabayashi et al., "Development of Non-invasive Fetal DNA Diagnosis from Maternal Blood," Prenatal Diagnosis, 15:74-77, 1995.
Thung et al. "Implementation of whole genome massively parallel sequencing for noninvasive prenatal testing in laboratories" Expert Review of Molecular Diagnostics. Jan. 2, 2015;15(1):111-24.
Toro et al. "Comparison of cell stabilizing blood collection tubes for circulating plasma tumor DNA" Clinical Biochemistry. Oct. 31, 2015;48(15):993-8.
Toro, "Detection of PIK3CA Mutations in Plasma Tumor DNA Circulating in Peripheral Blood of Breast Cancer Patients" Thesis submitted for the degree of Master of Science in Molecular and Cellular Biology. Johns Hopkins University, Baltimore, Maryland. Apr. 2014.
Tynan et al. Application of risk score analysis to low-coverage whole genome sequencing data for the noninvasive detection of trisomy 21, trisomy 18, and trisomy 13. Prenatal diagnosis, Jan. 1, 2015.
US Food and Drug Adminstration, "Draft Guidance for Industry: Pre-Storage Leukocyte Reduction of Whole Blood and Blood Components Intended for Transfusion, Vaccines." Blood & Biologics, available at: www.fda.gov/biologicsbloodvaccines/guidance complianceregulatoryinformation/guidances/blood/ucm076769.htm, last accessed Apr. 13, 2011.
Vandenberghe et al. "Non-invasive detection of genomic imbalances in Hodgkin/Reed-Sternberg cells in early and advanced stage Hodgkin's lymphoma by sequencing of circulating cell-free DNA: a technical proof-of-principle study" The Lancet Haematology. Feb. 28, 2015;2(2):e55-65.
Verweij et al. "European Non-Invasive Trisomy Evaluation (EU-NITE) study: a multicenter prospective cohort study for non-invasive fetal trisomy 21 testing" Prenatal Diagnosis, Oct. 1, 2013;33(10):996-1001.
Wagner "Free DNA—new potential analyte in clinical laboratory diagnostics" Biochem Med (Zagreb) 22(1): 24-38 (2012).
Wang D et al. Exploring Glycan Markers for Immunotyping and Precision-targeting of Breast Circulating Tumor Cells. Archives of medical research. Dec. 1, 2015.
Wang E et al. "Gestational age and maternal weight effects on fetal cell-free DNA in maternal plasma" Prenatal diagnosis. Jul. 1, 2013;33(7):662-6.
Wang P et al. "Sensitive detection of mono-and polyclonal ESR1 mutations in primary tumors, metastatic lesions and cell free DNA of breast cancer patients" Clinical Cancer Research. Oct. 23, 2015:clincanres-1534.
Wang Q et al. "Real-time PCR evaluation of cell-free DNA subjected to various storage and shipping conditions" Genetics and Molecular Research. Jan. 1, 2015;14(4):12797-804.
Wang Y et al. "Maternal mosaicism is a significant contributor to discordant sex chromosomal aneuploidies associated with noninvasive prenatal testing" Clinical chemistry. Jan. 1, 2014;60(1):251-9.
Werner et al. "Analytical Validation and Capabilities of the Epic CTC Platform: Enrichment-Free Circulating Tumour Cell Detection and Characterization" Journal of Circulating Biomarkers. 2015 4:3.
Wiebe et al., "Inhibition of Cell Proliferation by Glycerol" Life Sci., 1991, 48(16): 1511-7.
Wienzek-Lischka et al. "Noninvasive fetal genotyping of human platelet antigen-1a using targeted massively parallel sequencing" Transfusion Apr. 1, 2015.

(56) References Cited

OTHER PUBLICATIONS

Willems et al. "The first 3,000 non-invasive prenatal tests (NIPT) with the harmony test in Belgium and the Netherlands" Facts, Views & Vision in ObGyn. 2014;6(1):7.
Wong et al. "Optimizing blood collection, transport and storage conditions for cell free DNA increases access to prenatal testing" Clinical Biochemistry. Aug. 31, 2013;46(12):1099-104.
Woolcock et al. "Noninvasive prenatal testing." Australian Family Physician. Jul. 1, 2014;43(7):432.
Zhang, Yi et al., "Effect of Formaldehyde Treatment on the recovery of cell-free fetal DNA from Maternal Plasma at Different Processing Times" Clinic Chimica Acta 397, 60-64, 2008.
Zill et al. "Cell-free DNA next-generation sequencing in pancreatobiliary carcinomas" Cancer discovery. Oct. 1, 2015;5(10):1040-8.
Co-pending U.S. Appl. No. 12/689,370, filed Jan. 19, 2010, Published as 2010/0184069 A1 on Jul. 22, 2010.
Co-pending U.S. Appl. No. 12/704,030, filed Feb. 11, 2010, Published as 2010/0209930 on Aug. 19, 2010.
Co-pending U.S. Appl. No. 13/648,415, filed Oct. 10, 2012, Published as 2013-0034860 on Feb. 7, 2013.
Co-pending U.S. Appl. No. 14/071,969, filed Nov. 5, 2013, Published on Feb. 18, 2014 as 2014/0054508.
Co-pending U.S. Appl. No. 12/941,437, filed Nov. 8, 2010, Published as 2011/0111410A1 on May 12, 2011.
Co-pending U.S. Appl. No. 10/605,669, filed Oct. 16, 2003, Published on Jul. 15, 2004 as 2004/0137417.
Co-pending U.S. Appl. No. 12/850,269, filed Aug. 4, 2010, Published on Dec. 16, 2010 as 2010/0317107.
Co-pending U.S. Appl. No. 15/010,549, filed Jan. 29, 2016, Published on May 26, 2016 as 2016/0143268.
Co-pending U.S. Appl. No. 13/766,207, filed Feb. 13, 2013, Published on Mar. 20, 2014 as 2014/0080112.
Co-pending U.S. Appl. No. 14/153,204, filed Jan. 13, 2014, Published on Jul. 7, 2014 as 2014/0199681.
Co-pending U.S. Appl. No. 14/907,167, filed Jan. 22, 2016, Published on Jun. 23, 2016 as 2016/0174544.
Rykova et al., "Concentrations of Circulating RNA from Healthy Donors and Cancer Patients Estimated by Different Method," Ann. N.Y. Acad. Sci. (2006) vol. 1075, pp. 328-333.
The Scientific Committee on Cosmetic Product and Non-Food Products intended for Consumers "Opinion Concerning the Determination of Certain Formaldehyde Releasers in Cosmetic Products" Dec. 22, 2002, pp. 1-9.
Slocum et al., "Electron-Microscopic Cytochemical Localization of Diamine and polyamine oxidases in Pea and Maize Tissues," Planta vol. 183, pp. 443-450, (1991).
Miller "A Simple Salting Out Procedure for Extracting DNA from Human Nucleated Cells," Nucleic Acids Research vol. 16, p. 1215 (1988).
Butler "Genetics and Genomics of Core Short Tandem Repeat Loci Used in Human Identity Testing," Journal of Forensic Science, vol. 51, No. 2, pp. 253-265, Mar. 2006.
Brown "Effect of Blood Collection and Processing on Radioimmunoassay Results for Apolipoprotein B in Plasma" Clinical Chemistry, 36/9, 1662-1666, 1990.
Skidmore et al., "Characterization and Use of the Potent Ribonuclease Inhibitor Aurintricarboxylic Acid for the Isolation of RNA from Animal Tissues," Biochem Journal, 263, pp. 73-80 (1989).
May et al. "How Many Species Are There on Earth?," Science vol. 241 p. 1441-1449, 1988.
Modrek "Genome-wide Detection of Alternative Splicing in Expressed Sequences of Human Genes," Nucleic Acid Research, vol. 29, No. 13 pp. 2850-2859, (2001).
Passage from confidential document, Streck, Inc. Cell-Free DNA BCT 510(k) Premarket Notification, Sep. 19, 2012.
Su YH, Wang M, Aiamkitsumrit B, Brenner DE, Block TM. Detection of a K-ras mutation in urine of patients with colorectal cancer. Cancer Biomarkers. Jan. 1, 2005;1(2, 3):177-82.
Cannas A, Kalunga G, Green C, Calvo L, Katemangwe P, Reither K, Perkins MD, Maboko L, Hoelscher M, Talbot EA, Mwaba P. Implications of storing urinary DNA from different populations for molecular analyses. PloS one. Sep. 10, 2009;4(9):e6985.
Cherepanova A, Tamkovich S, Pyshnyi D, Kharkova M, Vlassov V, Laktionov P. Immunochemical assay for deoxyribonuclease activity in body fluids. Journal of immunological methods. Aug. 31, 2007;325(1):96-103.
S.H. Zhang et al.: "Genotyping of urinary samples stored with EDTA for forensic applications", Genetics and Molecular Research, vol. 11, No. 3, May 10, 2012, pp. 3007-3012, XP055291026, DOI: 10.4238/2012.
Antje Milde et al.: "Improved DNA typing of human urine by adding EDTA", Int. J Legal Med, Jan. 1, 1999, pp. 209-210, XP055291033.
Nicole T Vu et al.: "Genotyping for DQA1 and PM loci in urine using PCR-based amplification: Effects of sample volume, storage temperature, preservatives, and aging on DNA extraction and typing", Forensic Science International., vol. 102, No. 1, May 1, 1999, pp. 23-34.
Latifa El Bali et al.: "Comparative Study of Seven Commercial Kits for Human DNA Extraction from Urine Samples Suitable for DNA Biomarker-Based Public Health Studies", Journal of Biomolecular Techniques, Dec. 1, 2014.
Tong YK, Lo YD. Diagnostic developments involving cell-free (circulating) nucleic acids. Clinica Chimica Acta. Jan. 31, 2006;363(1):187-96.
Dean, (proceeding national Academy of Sciences (2002) vol. 99, pp. 5261-5266).
Alvarez et al., "Comparison of protein, microRNA, and mRNA yields using different methods of urinary exosome isolation for the discovery of kidney disease biomarkers," Kidney International 82:1024-1032 (2012).
Chutkan et al., "Quantitative and qualitative preparations of bacterial outer membrane vesicles," Methods Mol Biol 966:259-272 (2013).
Deatherage et al., "Membrane Vesicle Release in Bacteria, Eukaryotes, and Archaea: a Conserved yet Underappreciated Aspect of Microbial Life," Infection and Immunity 80(6):1948-1957 (2012).
Gheinani et al., "Improved isolation strategies to increase the yield and purity of human urinary exosomes for biomarker discovery," Scientific Reports, 8:3945, 17 pages (2018).
Ishizawa et al., "Simple procedure of DNA isolation from human serum," Nucleic Acids Research 19(20) (1991).
Kania et al., "Urinary proteases degrade albumin: implications for measurement of albuminuria in stored samples," Annals of Clinical Biochemistry 47:151-157 (2010).
Ramirez et al., "Technical challenges of working with extracellular vesicles," Nanoscale 10:881-906 (2018).
Zhou et al., "Collection, storage, preservation, and normalization of human urinary exosomes for biomarker discovery," Kidney Int. 69(8):1471-1476 (2006).
Ames et al.. An Appraisal of the "Vacutainer" System for Blood Collection, Ann. Clin. Biochem., 12:151-155 (1975).
Arikan, A comparison of the effect of methyl-beta-cyclodextrin on the osmotic fragility of ovine, bovine and human erythrocytes, Turk J. Vet. Anim. Sci., 27:383-387 (2003).
Colombo et al., Biogenesis, secretion, and intercellular interactions of exosomes and other extracellular vesicles, Annu. Rev. Cell Dev. Biol., 30:255-89 (2014).
Das et al. Effects of a novel cell stabilizing reagent on DNA amplification by PCR as compared to traditional stabilizing reagents, Acta Histochemica; 116(1):55-60 (2014).
De Miranda et al., Cyclodextrins and ternary complexes: technology to improve solubility of poorly soluble drugs, Br J. Pharm. Sci., 47(4):665-81 (2011).
Dhallan et al., A noninvasive test for prenatal diagnosis based on fetal DNA present in maternal blood: a preliminary study, The Lancet.; 369 (9560): 474-481 (2007).
Dumaswala et al., Improved red blood cell preservation correlates with decreased loss of bands 3, 4.1, acetylcholinestrase, and lipids in microvesicles, Blood, 87(4): 1612-6 (1996).
EP Application No. 10000518.0 (Patent No. EP2228453), Brief communication regarding Letter from the opponent 02 (Cenata) of Jun. 6, 2018 including exhibits, dated Jun. 14, 2018.

(56) References Cited

OTHER PUBLICATIONS

EP Application No. 10000518.0 (Patent No. EP2228453), Brief communication to Opponent 1 and Opponent 2 dated May 29, 2018 and Reply including exhibits of patent proprietor to notice(s) of opposition dated Apr. 26, 2018.
European Application No. 10704474.5, European Third Party Observations, mailed Aug. 30, 2016.
European Application No. 10000518.0, Communication of a notice of intervention including exhibits by Cenata GmbH, mailed Apr. 13, 2018.
European Application No. 10000518.0, Communication of a notice of opposition including exhibits, mailed Sep. 12, 2017.
European Application No. 10704474.5, European Patent Office Summons to Attend, mailed Jan. 27, 2016.
European Application No. 13706856.5, Communication of a notice of opposition including exhibits, mailed Mar. 28, 2018.
European Application No. 13706856.5, European Third Party Observations, mailed May 25, 2016.
Fernando et al., A new methodology to preserve the original proportion and integrity of cell-free fetal DNA in maternal plasma during sample processing and storage, 30(5):418-424 (2010).
Funasaki et al., Mechanisms and surface chemical prediction of imipramine-induced hemolysis suppressed by modified cyclodextrins, J. Pharm. Sci., 90(8):1056-65 (2001).
Greenwalt et al., Erythrocyte membrane vesiculation and changes in membrane composition during storage in citrate-phosphate-dextrose-adenine-1, Vox Sang., 47(4):261-70 (1984).
Grölz et al., Liquid biopsy preservation solutions for standardized pre-analytical workflows-venous whole blood and plasma, Curr. Pathobiol. Rep., 6(4):275-286 (2018).
György et al., Improved circulating microparticle analysis in acid-citrate dextrose (ACD) anticoagulant tube, Thromb Res., 133(2)1285-92 (2014).
Hallick et al., Use of Aurintricarboxylic Acid as in Inhibitor of Nucleases During Nucleic Acid Isolation, Nucleic Acid Research, 4:3055-3064 (1977).
Hanessian et al.. The Synthesis of functionalized cyclodextrins as scaffolds and templates for molecular diversity, Catalysis, and Inclusion Phenomena, J. Org. Chern., 60(15):4786-4797 (1995).
International Application No. PCT/US2018/056747, International Search Report and Written Opinion, dated Dec. 17, 2018.
International Application No. PCT/US2018/056747, International Preliminary Reporton Patentability, dated Apr. 30, 2020.
International Application No. PCT/US2010/023859, International Search Report and Written Opinion, dated Feb. 11, 2010.
International Application No. PCT/US2010/55815, International Search Report and Written Opinion, dated Nov. 8, 2010.
International Application No. PCT/US2013/025912, International Preliminary Report on Patentability, dated Apr. 25, 2014.
International Application No. PCT/US2013/025912, Written Opinion of the International Preliminary Examining Authority, dated Jan. 24, 2014.
International Application No. PCT/US2014/047551, International Preliminary Report on Patentability, dated Dec. 10, 2015.
International Application No. PCT/US2014/047551, International Search Report & Written Opinion, dated Oct. 23, 2014.
Irie et al., Cyclodextrin-induced hemolysis and shape changes of human erythrocytes in vitro, J. Pharmacobiodyn, 5(9):741-744 (1982).
Jodal et al., Investigation of the hemolytic effect of the cyclodextrin derivatives, Proceedings of the Fourth International Symposium on Cyclodextrins, 421-425, (1988).
Leclercq, Interactions between cyclodextrins and cellular components: Towards greener medical applications?, Beilstein J. Org. Chem., 12:2644-62 (2016).
Lee et al., The importance of standardization on analyzing circulating RNA, Mol. Diagn. Ther., 21(3):259-268 (2017).
Lo, Introduction: Plasma DNA and Urinary DNA, pp. 261-263, from Bruns et al. (eds.), Molecular Testing in Laboratory Medicine: Selections from Clinical Chemistry, 1998-2001, AACC Press (2002).
Loftsson et al., Cyclodextrins in drug delivery, Expert Opin. Drug Deliv., 2:335-351 (2005).
Loftsson et al., Self-association of cyclodextrins and cyclodextrin complexes, J. Pharm. Sci., 93(5):1091-1099 (2004).
Lutz et al., Release of spectrin-free vesicles from human erythrocytes during ATP depletion. I. Characterization of spectrin-free vesicles, J. Cell Biol., 73(3):548-60 (1977).
Mahammad et al., Cholesterol depletion using methyl-beta-cyclodextrin, Methods in Membrane Lipids, 91-102 (2015).
Makhro et al., Red cell properties after different modes of blood transportation, Front Physiol., 7:288 (2016).
Merriam-Webster's Medical Dictionary, p. 606, Springfield, MA: Merriam-Webster Incorporated (1995).
Motoyama et al., Effect of 2,6-di-O-methyl-alpha-cyclodextrin on hemolysis and morphological change in rabbit's red blood cells, Eur. J. Pharm. Sci., 29(2):111-9 (2006).
Motoyama et al., Involvement of lipid rafts of rabbit red blood cells in morphological changes induced by methylated beta-cyclodextrins, Biol. Pharm. Bull., 32(4):700-5 (2009).
Niei et al., Shedding light on the cell biology of extracellular vesicles, Nat. Rev. Mol. Cell Biol., 19(4):213-228 (2018).
Notice of Opposition to a European patent dated Apr. 24, 2019, received from the European Patent Office Application No. 02761478. 3.
Oh et al., Damage to red blood cells during whole blood storage, J. Trauma Acute Care Surg., 89(2):344-350 (2020).
Ohtani et al., Differential effects of alpha-, beta-and gamma-cyclodextrins on human erythrocytes, Eur. J. Biochem., 186(1-2):17-22 (1989).
Perakis et al., Emerging concepts in liquid biopsies, BMC Med., 15(1):75 (2017).
Rajewski et al., Pharmaceutical applications of cyclodextrins. 2. In vivo drug delivery, J. Pharm. Sci., 85(11):1142-1169 (1996).
Raposo et al., Extracellular vesicles: exosomes, microvesicles, and friends, J. Cell Biol., 200(4):373-83 (2013).
Róka et al.. Evaluation of the cytotoxicity of (Alpha)-cyclodextrin derivatives on the caco-2 cell line and human erythrocytes, molecules, 20(11):20269-85 (2015).
Salvianti et al.. The pre-analytical phase of the liquid biopsy, N. BiotechnoL, 55:19-29 (2020).
Smit et al., Semiautomated DNA Mutation Analysis Using a Robotic Workstation and Molecular Beacons, Clinical Chemistry, 47:739-744 (2001).
Streck et al., 1-XP55419765A, Product Summary: Cell-Free DNA(Trademark) BCT, (2009).
Swarup et al., Circulating (cell-free) Nucleic Acids—A Promising, Non-lnvasive Tool for Early Detection of Several Human Diseases, FEBS Letters, 481:795-799 (2007).
Szarvas et al., Determination of Endogenous Formaldehyde Level in Human Blood and Urine by Dimedone-14C Radiometric Method, J. Radioanal. Nucl. Chern., Letters; 106, 357-367 (1986).
Torrano et al., Vesicle-MaNiA: extracellular vesicles in liquid biopsy and cancer, Curr. Opin. Pharmacol., 29:47-53 (2016).
U.S. Provisional Application filed on Feb. 3, 2017, by Noble et al., U.S. Appl. No. 62/454,451.
U.S. Provisional Application filed on Feb. 3, 2017, by Noble et al., U.S. Appl. No. 62/454,460.
Uekama et al., Protective effects of cyclodextrins on drug-induced hemolysis in vitro, J. Pharmacobiodyn., 4(2):142-4 (1981).
Wang et al., Lipoprotient Lipase: from gene to obesity, Am. J. Physiol. Endocrinol. Met., 297(2):E271-E288 (2009).
Weisz et al., Protection of erythrocytes against hemolytic agents by cyclodextrin polysulfate, Biochem Pharmacol., 45(5):1011-6 (1993).
What are the regulatory Definitions for "Ambient", "Room Temperature" and "Cold Chain" (https://www.gmp-compliance.org/gmp-news/what-are-the-regulatory-definitions-for-ambient-room-temperature-and-cold-chain) (2017).
Wolf, The nature and significance of platelet products in human plasma, Br. J. Haematol., 13(3):269-88 (1967).
Wong et al., The role of physical stabilization in whole blood preservation, Sci. Rep., 6:21023 (2016).
Yoshida et al., Red blood cell storage lesion: causes and potential clinical consequences, Blood Transfus., 17(1):27-52 (2019).

(56) References Cited

OTHER PUBLICATIONS

Zhou et al., Cyclodextrin functionalized polymers as drug delivery, Polymer Chemistry, 1:1552-1559 (2010).
Supplementary Partial European Search Report from European Application No. EP 17 84 2131 dated Mar. 16, 2020.
Augustus et al., The art of obtaining a high yield of cell-free DNAfrom urine, PLoS ONE, 15(4): e0231058:1-22 K2020).
Bloom et al., Cell-free DNA and active rejection in kidney allografts, J. Am. Soc. Nephrol., 28(7):2221-2232 (2017).
Boffa et al., Cellular expression of PD-L1 in the peripheral blood of lung cancer patients is associated with worse survival, Cancer Epidemiol. Biomarkers Prev., 26(7):1139-1145 (2017).
Camunas-Soler et al., Noninvasive prenatal diagnosis of single-gene disorders by use of droplet digital PCR, Clin. Chem, 64(2):336-345 (2017).
Chang et al., Review of the clinical applications and technological advances of circulating tumor DNA in cancer monitoring, The Clin. Risk Manag., 13:1363-1374 (2017).
Chu et al., ESR1 mutations in circulating plasma tumor DNA from metastatic breast cancer patients, Clin. Cancer Res, 22(4):993-999 (2016).
Clausen et al., Noninvasive fetal RhD genotyping, Transfusion and Apheresis Science, 50:154-162 (2014).
Dessel et al., Application of circulating tumor DNA in prospective clinical oncology trials—standardization of preanalytical conditions, Mol. Oncol., 11(3):295-304 (2017).
Diaz et al., Performance of streck cfDNA blood collection tubes for liquid biopsy testing, PLoS One, 11(11):e0166354 K2016).
Gogoi et al., Development of an automated and sensitive microfluidic device for capturing and characterizing circulating tumor cells (CTCs) from clinical blood samples, PLoS One, 11(1):e0147400 (2016).
Greene et al., Chromosomal instability estimation based on next generation sequencing and single cell genome wide copy number variation analysis, PLoS One, 11(11):e0165089 (2016).
Grskovic et al., Validation of a clinical-grade assay to measure donor-derived cell-free DNA in solid organ transplant recipients, J. Mol. Diagn., 18(6):890-902 (2016).
Herrera et al., Cell-free DNA, inflammation, and the initiation of spontaneous term labor, Am. J. Obstet. Gynecol., 217(5):583.e1-583.e8 (2017).
Hrebien et al., Reproducibility of digital PCR assays for circulating tumor DNA analysis in advanced breast cancer, PLoS One, 11 (10):e0165023 (2016).
Hulten et al., Non-invasive prenatal diagnosis: an epigenetic approach to the detection of common fetal chromosome disorders by analysis of maternal blood samples, Circulating Nucleic Acids In Plasma and Serum, 133-142(2011).
Hyland et al., Non-invasive fetal RHD genotyping for RhD negative women stratified into RHD gene deletion or variant groups: comparative accuracy using two blood collection tube types, Pathology, 49(7):757-764 (2017).
Kidess-Sigal et al., Enumeration and targeted analysis of KRAS, BRAF and PIK3CA mutations in CTCs captured by a label-free platform: comparison to ctDNA and tissue in metastatic colorectal cancer, Oncotarget, 7(51):85349-85364 (2016).
Kotsopoulou et al., Non-invasive prenatal testing (NIPT): limitations on the way to become diagnosis, Diagnosis, 2(3): 141-158 (2015).
Krol et al., Detection of circulating tumour cell clusters in human glioblastoma, Br. J. Cancer, 119(4):487-491 (2018).
Lee et al., Quantitation of genomic DNA in plasma and serum samples: higher concentrations of genomic DNA found in serum than in plasma, Transfusion, 41:276-282 (2001).
Lench et al., The clinical implementation of non-invasive prenatal diagnosis for single-gene disorders: challenges and progress made, Prenat. Diagn., 33(6):555-62 (2013).
Lewis et al., Detecting cancer biomarkers in blood: challenges for new molecular diagnostic and point-of-care tests using cell-free nucleic acids, Expert Rev. Mol. Diagn., 15(9): 1187-200 (2015).

Locke et al., DNA Methylation Cancer Biomarkers: Translation to the Clinic, Frontiers in Genetics, 10(1150): 1-22 K2019).
Markus et al., Evaluation of pre-analytical factors affecting plasma DNA analysis, Sci. Rep., 8(1):7375 (2017).
Marrinucci et al., Cytomorphology of circulating colorectal tumor cells:a small case series, J. Oncol., 2010:861341 K2010).
Mellert et al., Development and clinical utility of a blood-based test service for the rapid identification of actionable mutations in non-small cell lung carcinoma, J. Mol Diag., 19(3):404-416 (2017).
Murugesan et al., Investigation of Preanalytical Variables Impacting Pathogen Cell-Free DNA in Blood and Urine, Journal of Clinical Microbiology, 57(11):1-13 (2019).
Parpart-Li et al., The effect of preservative and temperature on the analysis of circulating tumor DNA, Clinical Cancer Research, 23(10):2471-2477 (2017).
Pertl et al., Detection of male and female fetal DNA in maternal plasma by multiplex fluorescent polymerase chain Yeaction amplification of short tandem repeats, Hum. Genet., 106:45-49 (2000).
Phillips et al., Optical quantification of cellular mass, vol. and density of circulating tumor cells identified in an ovarian cancer patient, Front Oncol., 2:72 (2012).
Phillips et al., Quantification of cellular vol. and sub-cellular density fluctuations: comparison of normal peripheral blood cells and circulating tumor cells identified in a breast cancer patient, Front. Oncol, 2:96 (2012).
Qin et al., Stabilization of cfDNA in Urine Using a Preservative Reagent During Sample Processing, Transport, and Storage, presented at Biofluid Biopsies & High-Value Diagnostics on Nov 16-17, and the Molecular Medicine Tri-Conference in February, Boston (2015).
Risberg et al., Effects of collection and processing procedures on plasma circulating cell-free DNA from cancer patients, J. Mol. Diagn., 20(6):883-892 (2018).
Rodriguez-Lee et al., Effect of blood collection tube type and time to processing on the enumeration and high-content characterization of circulating tumor cells using the high-definition single-cell assay, Arch. Pathol. Lab. Med., 142(2): 198-207 (2017).
Sacher et al., Prospective validation of rapid plasma genotyping for the detection of EGFR and KRAS mutations in advanced lung cancer, JAMA Oncol., 2(8):1014-22 (2016).
Scher et al., Association of AR-V7 on circulating tumor cells as a treatment-specific biomarker with outcomes and survival in castration-resistant prostate cancer, JAMA. Oncol, 2(11):1441-1449 (2016).
Sherwood et al., Optimised pre-analytical methods improve KRAS mutation detection in circulating tumour DNA KctDNA) from patients with non-small cell lung cancer (NSCLC), PLoS One, 11(2):e0150197 (2016).
Smith et al., Targeted mutation detection in breast cancer using MammaSeq (Trademark), Breast Cancer Research, 21(1):22 (2019).
Thompson et al., Detection of therapeutically targetable driver and resistance mutations in lung cancer patients by next-generation sequencing of cell-free circulating tumor DNA, Clin. Cancer Res , 22(23):5772-5782 (2016).
Trigg et al., Factors that influence quality and yield of circulating-free DNA: a systematic review of the methodology Titerature, Heliyon, 4(7):e00699 (2018).
Veldore et al., Validation of liquid biopsy: plasma cell-free DNA testing in clinical management of advanced non-small cell lung cancer, Lung Cancer: Targets and Therapy, 9:1-11 (2018).
Wollison et al., Blood collection in cell-stabilizing tubes does not impact germline DNA quality for pediatric patients, PLoS One, 12(12):e0188835 (2017).
Yee et al., A novel approach for next-generation sequencing of circulating tumor cells, MoL Genet. Genomic Med., 4(4):395-406 (2016).
Zhang et al., Detection and characterization of circulating tumour cells in multiple myeloma, J. Circ. Biomark., 5:10 K2016).
Maunier et al., Can stabilization of whole blood samples with Cytochex (Trademark) allow test batching of CD55 and CD59 deficiency flow cytometry analysis?, Cellquant-Redquant CD55/CD59, 1-8 (2012).
McCoy, Ch. 10: Preparation of cells from blood, Methods in Cell Biology, 63 (2001).

(56) References Cited

OTHER PUBLICATIONS

Miller-Lindholm et al., Streck cell preservative preserves bone marrow specimens, Streck Cell Preservative Application Note Issue 1, 320024-2, 1-4 (2004).
Minear et al., Global perspectives on clinical adoption of NIPT, Prenat. Diagn., 35(10):959-967 (2015).
Nace et al., Evaluation of Streck tissue fixative, a nonformalin fixative for preservation of stool samples and subsequent parasitologic examination, J. Clin. Microbiology, 37(12):4113-4119 (1999).
Nigam et al., Detection of fetal nucleic acid in maternal plasma: A novel noninvasive prenatal diagnostic technique, JIMSA., 25(3):199-200 (2012).
Norton et al., A new blood collection device minimizes cellular DNA release during sample storage and shipping when compared to a standard device, J. Clin. Laboratory Analysis, 27:305-311 (2013).
O'Leary et al., The importance of fixation procedures on DNA template and its suitability for solution-phase polymerase chain reaction and PCR in situ hybridization, Histochemical Journal, 26:337-346 (1994).
Parackal et al., Comparison of Roche Cell-Free DNA collection Tubes (Registered) to Streck Cell-Free DNA BCT (Registered) s for sample stability using healthy volunteers, Pract. Lab. Med., 16:e00125 (2019).
Patterson et al., Fixation for in situ molecular analysis. B.K. Patterson (ed.), Techniques in quantification and localization of gene expression, 23-34 (2000).
Pietrzak-Johnston et al., Evaluation of commercially available preservatives for laboratory detection of helminths and protozoa in human fecal specimens, J. Clin. Microbiology, 38(5): 1959-1964 (2000).
Qin et al., Evaluation of a single spin protocol for plasma DNA isolation from blood collected & stored in cell-free Dna BCT, Annual Meeting of American College of Medical Genetics and Genomics (2016).
Raptis et al., Quantitation and characterization of plasma DNA in normals and patients with systemic lupus erythematosus, J. Clin. Invest., 66:1391-1399 (1980).
Rintu et al., MRCH, Does formaldehyde increase cell free DNA in maternal plasma specimens?, Laboratory Med., 47(4):286-292 (2016).
RNAlater product information, Sigma-aldrich technical bulletin (2016).
Roche product alert notice—AA-harmony test-QN-SEQ-2017-003 (2017).
Saxton et al., Effect of ex vivo storage on human peripheral blood neutrophil expression of CD11b and the stabilizing effects of Cyto-Chex, J. Immunol. Methods, 214:11-17 (1998).
Springer et al., Evaluation of a new reagent for preserving fresh blood samples and its potential usefulness for internal quality controls of multichannel hematology analyzers, Am. J. Clin. Pathol., 111:387-396 (1999).
Stokowski et al., Evaluation of automated cell-free DNA extraction methods with the harmony(Registered) prenatal test, Roche Sequencing Solutions, Roche Diagnostics, Inc. (2018). pp. 1-3.
Strom et al., Improving the positive predictive value of non-invasive prenatal screening (NIPS), PLOS one, 12(3): e0167130 (2017).
Taylor-Phillips et al., Accuracy of non-invasive prenatal testing using cell-free DNA for detection of down, Edwards and patau syndromes: a systematic review and meta-analysis, BMJ. Open., 6(1):e010002 (2016).
Truett et al., Efficacy of cyto-chex blood preservative for delayed manual CD4 testing using dynal T4 quant CD4 test among HIV-infected persons in Zambia, J. Acquir. Immune Defic. Syndr., 41 (2): 168-174 (2006).
Tsui et al., Stability of endogenous and added RNA in blood specimens, serum, and plasma, Clin. Chem., 48:1647-1653(2002).
Turpen et al., A reagent for stabilizing blood samples, American Clinical Laboratory, 15(8):30-31 (1996).
Utting et al., Detection of tumor genetic alterations of bladder carcinomas in body fluids depends on sample treatment before DNA isolation, 906:67-71 (2000).
Warrino et al., Absolute count data from streck cell preservative treated cells, Streck Cell Preservative Application Note Issue 2, 320520-1, 1-2 (Date Unknown). 2014.
Warrino et al., Blood specimens stable in cyto-chex(Registered) BCT at elevated temperatures, Application Note, Issue 3, 20547-2, 1-4 (2006).
Warrino et al., Cyto-chex BCT stabilizes light scatter and cell morphology, Application Note, Issue 2, 320523-1, 1-4 (2005).
Warrino et al., Cyto-chex BCT stabilizes whole blood for seven days for immunophenotyping by flow cytometry, Application Note, Issue 1, 320517-4, 1-2 (2004).
Warrino et al., Cyto-chex(Registered) BCT allows for accurate T-cell counts by flow cytometry 14 days post sample collection, Application Note, Issue 4, 320563-1, 1-2 (Date Unkown). 2005.
Warrino et al., Cyto-Chex(Registered) blood collection tube stabilizes samples stored at elevated temperatures for flow cytometry analysis, Streck, Omaha, NE 68128,1 (Date Unknown). 2014.
Warrino et al., Stabilization of white blood cells and immunologic markers for extended analysis using flow cytometry, J. Immunol. Methods., 305:107-119 (2005).
Warrino, Cyto-chex BCT, not cyto-chex, should be used for preservation of CD4 cell counts, JAIDS., 43(4):503-504 (2006).
Weeks, How one laboratory reduced weekend flow cytometry staffing, Clinical Lab Products, 1-4 (2003).
Wijk et al., Detection of apoptotic fetal cells in plasma of pregnant women, Clin. Chem., 46(5):729-731 (2000).
World health organization. Diagnostic imaging and laboratory technology, Use of anticoagulants in diagnostic Taboratory investigations, World Health Organization (2002).
Zhong et al., Presence of mitochondrial tRNA(Leu(UUR)) A to G 3243 mutation in DNA extracted from serum and plasma of patients with type 2 diabetes mellitus, J. Clin. Pathol., 53:466-469 (2000).
Ziegler et al., Circulating DNA: a new diagnostic gold mine?, Cancer Treat Rev., 28:255-271 (2002).
Alidousty et al., Comparison of blood collection tubes from three different manufacturers for the collection of cell-free DNA for liquid biopsy mutation testing, J. MoL Diagnostics, 19(5)1801-804 (2017).
Amicucci et al., Prenatal diagnosis of myotonic dystrophy using fetal DNA obtained from maternal plasma, Clin. Chem., 46(2)1301-302 (2000).
Amitani et al., Allantoin ameliorates chemically-induced pancreatic (Beta)-cell damage through activation of the imidazoline I3 receptors, Peer J., 3:e1105 (2015).
Ammerlaan et al., Method validation for preparing serum and plasma samples from human blood for downstream proteomic, metabolomic, and circulating nucleic acid-based applications, Biopreserv. Biobank., 12(4):269-80 (2014).
Anitua, Plasma rich in growth factors: preliminary results of use in the preparation of future sites for implants, Int. J. Oral Maxillofac Implants, 14(4):529-35 (1999).
Anker et al., Circulating nucleic acids In plasma and serum as a noninvasive investigation for cancer: Time for large-scale clinical studies?, Int. J. Cancer, 103:149-152 (2003).
Ashoor et al., Fetal fraction in maternal plasma cell-free DNA at 11-13 weeks' gestation: relation to maternal and fetal characteristics, Ultrasound Obstet, Gynecol., 41:26-32 (2013).
Banfi et al., The role of ethylenediamine tetraacetic acid (EDTA) as in vitro anticoagulant for diagnostic purposes, Clin. Chem. Lab. Med., 45(5):565-576 (2007).
Barra et al., EDTA-mediated inhibition of DNases protects circulating cell-free DNA from ex vivo degradation in blood samples, Clinical Biochemistry, 48:976-81 (2015).
Benachi et al., Impact of formaldehyde on the in vitro proportion of fetal DNA in maternal plasma and serum, Clin. Chem., 51(1):242-244 (2005).
Bergholiz et al., Confirmation of equivalence of one-spin and two-spin protocols for plasma isolation from Lbgard(Registered) blood tubes, Biomatrica., (2018).
Boddy et al., Prospective study of quantitation of plasma DNA levels in the diagnosis of malignant versus benign prostate disease, Clinical Cancer Research, 11 (4): 1394-1399 (2005).

(56) References Cited

OTHER PUBLICATIONS

Brown et al., A novel flow cytometry stimulation assay using cyto-ches (Registered) BCT tubes for use in clinical trials, Flow Contract Site Laboratory, 1 (2011).
Campbell et al., Analytical and biological considerations in the measurement of cell-associated CCR5 and CXCR4 mRNA and protein, Clin. Vaccine Immun., 17(7): 1148-1154 (2010).
Catellier et al., Atherosclerosis risk in communities (ARIC) carotid MRI flow cytometry study of monocyte and platelet markers: intraindividual variability and reliability, Clinical Chemistry, 54(8): 1363-1371 (2008).
Cell-free DNA collection tube roche (2016). pp. 1-2.
Chan et al., Size distributions of maternal and fetal DNA in maternal plasma, Clinical Chemistry, 50(1):88-92 (2004).
Chiu et al., Effects of blood-processing protocols on fetal and total DNA quantification in maternal plasma, Clin. Chem., 47(9): 1607-1613 (2001).
Davis et al., Stability of immunophenotypic markers in fixed peripheral blood for extended analysis using flow cytometry, J. Immunol. Methods, 363:158-165 (2011).
European Application No. 16199783, European Search Report and Opinion, dated Feb. 17, 2017.
European Application No. 19186944, European Search Report and Opinion, dated Oct. 17, 2019.
Fan et al., Analysis of the size distributions of fetal and maternal cell-free DNA by paired-end sequencing, Clinical Chemistry, 56(8):1279-1286 (2010).
Fan et al., Noninvasive diagnosis of fetal aneuploidy by shotgun sequencing DNA from maternal blood, PNAS., 105(42):16266-16271 (2008).
Fiebelkorn et al., Clinical evaluation of an automated nucleic acid isolation system, Clin. Chem., 48(9): 1613-1615 (2002).
Finning et al., The use of maternal plasma for prenatal RhD blood group genotyping, Methods Mol Biol., 496:143-57 (2009).
Fleischhacker et al., Methods for isolation of cell-free plasma DNA strongly affect DNA yield, Clinica. Chimica. Acta., 412:2085-2088 (2011).
Fomovsky et al., Centrifuge-free isolation of liquid plasma from clinical samples from whole blood, Pall Life Sciences (2012).
Foy et al., Emerging homogeneous technologies for bioanalysis, Clin. Chem., 47(6)990-100 (2001).
Francis et al., Rapid single step method for flow cytometric detection of surface and intracellular antigens using whole blood, Cytometry, 25:58-70 (1996).
Gahlawat et al., Evaluation of storage tubes for combined analysis of circulating nucleic acids in liquid biopsies, Int. J. Mol. Sci., 20(3):704 (2019).
Greer et al., PCR amplification from paraffin-embedded tissues, Am. J. Clin. Pathol., 95(2):117-124 (1991).

Harmony prenatal test—IVD Kit—P/N 08011281001 (FGK1002)—Instructions for use, 31 pages, Retrieved from the Interneton or around Jul. 17, 2018.
Holodniy et al., Determination of human immunodeficiency virus RNA in plasma and cellular viral DNA genotypic zidovudine resistance and viral load during zidovudine-didanosine combination therapy, J. Virology, 69(6):3510-3516 (1995).
Jundi et al., Streck cell preservative(Trademark) preserves fine needle aspiration samples for immunophenotyping by flow cytometry, Streck, 1-3 (2021).
Jung et al., Changes in concentration of DNA in serum and plasma during storage of blood samples, Clin. Chem., 49 6 Pt 1:1028-1029 (2003).
Khosrotehrani et al., Fetal cell-free DNA circulates in the plasma of pregnant mice: relevance for animal models of fetomatemal trafficking, Human Reproduction, 19(11):2460-2464 (2004).
Kodym et al.. Determination of radiation-induced DNA strand breaks in individual cells by non-radioactive labelling of 3' OH ends, Int. J. Radiat. Biol., 68(2):133-139 (1995).
Lambert et al., Male microchimerism in healthy women and women with scleroderma: cells or circulating DNA? A quantitative answer, Blood, 100(8):2845-2851 (2002).
Leal-Klevezas et al., Antifreeze solution improves DNA recovery by preserving the integrity of pathogen-infected blood and other tissues, Clin. Diagnostic Laboratory Immun., 7(6):945-946 (2000).
Lee et al., Effect of platelet-associated virus on assays of HIV-1 in plasma, Science, 262:1585-1586 (1993).
Lehmann et al., Characterization and chemistry of imidazolidinyl urea and diazolidinyl urea, Contact Dermatitis, 54(1):50-58 (2006).
Lo et al., Commentary: fetal-derived paternally inherited genetic markers in maternal plasma, from molecular testing in laboratory medicine, AACC Press, 264-265 (2002).
Lo et al., Noninvasive prenatal diagnosis of fetal chromosomal aneuploidies by maternal plasma nucleic acid analysis Clin. Chem., 54(3):461-466 (2008).
Lo et al., Prenatal diagnosis of fetal RhD status by molecular analysis of maternal plasma, N Engl. J. Med., 1734-1738(1998).
Lo et al., Prenatal diagnosis: progress through plasma nucleic acids, Nature Reviews Genetics, 8:71-77 (2007).
Lo et al., Rapid clearance of fetal DNA from maternal plasma, Am. J. Hum. Genet., 64:218-224 (1999).
Lo, Fetal DNA in maternal plasma/serum: the first 5 years, Pediatr. Res., 53(1 ):16-17 (2003).
Lui et al., Circulating DNA in plasma and serum: Biology, Preanalytical issues and diagnostic applications, Clin. Chern. Lab. Med., 40(10):962-968 (2002).
Lui et al., Predominant hematopoietic origin of cell-free DNA in plasma and serum after sex-mismatched bone marrow transplantation, Clinical Chemistry, 48(3):421-427 (2002).
Luk et al., CTC-mRNA (AR-V7) Analysis from Blood Samples—Impact of Blood Collection Tube and Storage Time, Int. J. Mol. Sci., 18(5):1047 (2017).

STABILIZATION OF NUCLEIC ACIDS IN URINE

TECHNICAL FIELD

The present teachings relate to a urine preservative composition for stabilization of cell-free nucleic acid in a urine sample, a method for preserving a urine sample and a preservative delivery vessel.

BACKGROUND

Detection of circulating cell-free DNA (cfDNA) in blood plasma derived from tumor, fetus and transplanted organs has been well documented. See U.S. Patent Applications 2014/0080112 and 2010/0184069 incorporated by reference herein. These circulating cfDNAs can pass from the blood through the kidney barrier into urine. The obvious advantages and non-invasive nature of urine sampling makes urine a useful source of fetal and tumor DNA for the development of noninvasive prenatal and cancer diagnostic and prognostic tests, in addition to detection and identification if other disease states. However, the inherent instability of cfDNA in urine hinders its clinical utility. Nucleated cells in urine can also release genomic nucleic acids into urine leading to an increased nucleic acid background during sample processing and storage.

The discovery of cell-free nucleic acids in the circulation has opened up new opportunities for non-invasive diagnostic applications in cancer testing and prenatal diagnosis (Tong Y K and Lo Y M D. Diagnostic developments involving cell-free (circulating) nucleic acids. *Clinica Chimica Acta* 2006; 363:187-196). Since the confirmation of cfDNA presence in urine, there has been much interest in the potential utility of urinary DNA for clinical diagnostic development. (Botezatu I, Serdyuk O, Potapova G, et al. Genetic analysis of DNA excreted in urine: a new approach for detecting specific genomic DNA sequences from cells dying in an organism. *Clinical Chemistry* 2000; 46:1078-1084.) The main advantage of urine over other body fluids (e.g., blood) is that urine sampling is truly non-invasive and it can be obtained safely and in large amounts with very limited training. When employing urinary cfDNA, however, it is important to minimize release of cellular DNA from nucleated cells and stabilize cfDNA following urine collection since cfDNA targets are present at low quantities and degrade rapidly. (Su Y H, Wang M J, Aiamkitsumrit B, et al. Detection of a K-ras mutation in urine of patients with colorectal cancer. *Cancer Biomarkers* 2005; 1; 177-182.) (Cannas A, Kalunga G, Green C, et al. Implications of Storing Urinary DNA from Different Populations for Molecular Analyses. *PLoS ONE* 2009; 4: e6985). Urine conditions (i.e. pH, nuclease activity) are markedly different from those of blood. On average nuclease activity in fresh urine is greater than that in blood plasma. (Cherepanova A, Tamkovich S, Pyshnyi D, et al. Immunochemical assay for deoxyribonuclease activity in body fluids. *Journal of immunological methods.* 2007 Aug. 31; 325(1):96-103.) All articles are incorporated by reference herein.

Effective stabilization of the nucleated blood cells in urine alone is not sufficient to effectively stabilize the native cell free DNA compliment in fresh urine. Inhibition of the significantly higher nuclease activity in urine as compared to blood plasma is critical to the effective stabilization. Therefore, requirements for effective stabilization of the native cell free DNA in urine samples are multi-fold.

Effective stabilization of cell free-DNA in urine requires stabilization of nucleated blood cells in urine, quenching of damaging free formaldehyde that may be present from stabilizing/preserving agents and blocking of the high nuclease activity in urine. There is a need for nucleated blood cell stabilization to reduce the level of contaminating genomic DNA to the overall DNA yield. There is a need for a preserving/stabilizing agent which does not compromise or destroy the structural integrity of the actionable mutations in the cell free DNA and or ctDNA due to free formaldehyde. There is a need for blocking enzymatic active (i.e. DNase activity) in fresh urine to prevent the enzymatic activity that will rapidly hydrolyze nucleic acids. Thus, there is a need for a preservative reagent that can preserve the original proportion and integrity of cfDNA in urine post specimen collection.

It is also necessary to address pre-analytical issues that arise during the time between urine collection and cfDNA isolation. These include delays in urine processing and specimen storage temperature. Such conditions may cause cellular DNA contamination and subsequently alter cfDNA levels circulating in urine. Thus, in order to obtain reproducible results, it is essential to standardize the pre-analytical procedure for urine sample handling. cfDNA preservation and stabilization in urine should be an integral part of the non-invasive diagnostic test development using urine as the source of genetic material. Thus, there is a need for a urine preservation method and preservation delivery vessel that can maintain the cfDNA concentration in urine post specimen collection. There is a need for a urine preservation method and preservation delivery vessel that offers the benefit of preserving urine cellular material that may later be processed and the nucleic acids isolated for molecular diagnostic analysis.

SUMMARY OF THE INVENTION

The present teachings contemplate a urine preservative composition for stabilization of cell-free DNA in a urine sample. The present teachings provide for stabilization of nucleated blood cells in urine. The present teachings further provide for quenching substantially all available free formaldehyde that may be present from stabilizing/preserving agents which release formaldehyde. The present teachings provide for blocking of nuclease activity. Thus, the present teachings provide a preservative reagent that can preserve the original proportion and structural integrity of cfDNA in urine post specimen collection.

The present teachings contemplate a method that can stabilize cfDNA in urine and minimize the post-sampling urinary DNA background for an extended period of time at various storage temperatures. This new methodology provides clinical laboratories with great flexibility and convenience in urine sample processing, handing and storage for urinary nucleic acid testing as it eliminates the necessity for immediate separation of supernatant after urine collection and refrigerating/freezing urine for transport.

Such a method may comprise a step of dispensing into a specimen container a predetermined amount of a urine preservative by removing the urine preservative from a sealed vessel. The method may also include a step of contacting the urine preservative with a urine sample. The method may also include the step of sealing the specimen container with the urine sample and the urine preservative contained within it. The step may also include causing the sealed specimen container to be shipped to a clinical laboratory for analysis of the urine sample. The urine sample, upon being preserved, may be capable of analysis after a period at least 168 hours or at least 7 days has elapsed.

There may be a urine collection step of obtaining a urine sample from a patient into a specimen container prior to the contacting step. The urine sample may be a random specimen, a first morning specimen, a midstream clean catch specimen, a timed collection specimen, a catheter collection specimen, or a suprapubic specimen. The urine sample may be preserved at the collection site, for example a doctor's office. The method may include a step of transporting the preserved urine sample to another site, for example a clinical laboratory at which analysis will occur. The clinical laboratory may perform urinalysis testing on the preserved urine sample and report the results. The preserved urine sample may be processed for isolating circulating nucleic acids. The preserved urine sample may be processed for isolating any circulating tumor cells, minimal residual disease and pathogens for diagnostic analysis.

The method may include a preservative delivery vessel for dispensing into a specimen container a predetermined amount of a urine preservative. The preservative delivery vessel may include a dispensing nozzle portion that includes a sealed tip that is capable of being ruptured to define a nozzle opening. The preservative delivery vessel may include an elongated hollow barrel portion in fluid communication with the dispensing nozzle portion. The barrel portion may contain a bodily fluid preservative composition. The barrel portion may have an initial internal volume and a flexible wall structure that is capable of being squeezed manually by a user (e.g. in the absence of any assistive tool) for reducing the initial internal volume to a smaller volume and applying pressure to advance the preservative composition towards and through the nozzle opening after the sealed tip is ruptured.

The teachings herein further contemplate that the methods disclosed herein result in preserving circulating cell-free DNA in urine over a wide range of dilution ratios within temperature fluctuations that can occur during urine sample handling, storage and transportation. The urine sample preservation method and preservative delivery vessel provide a method for obtaining high quality stabilized urinary cell-free DNA for clinical diagnostics development and application.

DETAILED DESCRIPTION

Figure 1:
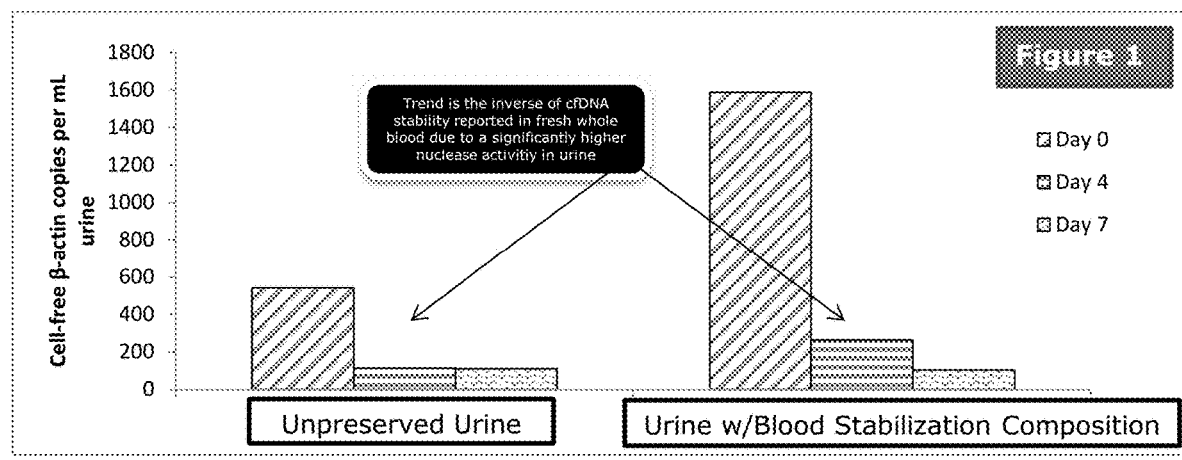
FIG. 1 compares the results of unpreserved urine samples and urine samples treated with a composition typically used for blood stabilization including 0.17% $K_3EDTA$.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

This application claims the benefit of the filing date of U.S. Provisional Application No. 62/128,774, filed Mar. 5, 2015. The entirety of the contents of that application are hereby incorporated by reference for all purposes.

The urine preservative composition provides for stabilization of cell-free nucleic acid in a urine sample. The urine sample includes nucleic acids which may be include one or more of cell free nucleic acids, circulating tumor nucleic acids, cellular nucleic acids, DNA, RNA, microRNA (miRNA), or messenger RNA (mRNA). The urine preservative composition may include one or more stabilizing/preserving agents. The one or more stabilizing/preserving agents may be formaldehyde releasing agents. The urine preservative composition may include one or more formaldehyde quenching agents. The urine preservative composition may include one or more nuclease inhibitors. The urine preservative composition may comprise a stabilizing/preserving agent, a formaldehyde quenching agent and a nuclease inhibitor in an amount that is greater than the amount required for stabilizing cell-free nucleic acid in blood. Considering the relatively minor in nuclease activity in urine, it is surprising that such a significant increase in nuclease inhibitor (as compared to blood stabilizers) is required to compensate for the increase in nuclease activity.

The method may include contacting the urine sample while within the sample specimen container with a urine preservative composition that includes a formaldehyde releasing agent and a quenching agent. The quenching agent may be present in an amount sufficient to react with any free formaldehyde so that the free formaldehyde (e.g., all of the free formaldehyde) reacts to form a reaction product that is inert. The urine preservative composition may also include a nuclease inhibitor in an amount significantly greater than that utilized for blood stabilization, much more than would be expected considering the minor increase in nuclease activity in urine as compared to blood.

Effective stabilization of the nucleated blood cells present in urine serves to prevent contamination of the native cell free DNA compliment present in fresh urine. Nucleated blood cell stabilization reduces the level of contaminating genomic DNA in the overall DNA yield. One of the most significant challenges with respect to the detection of actionable mutations in cell free DNA and or ctDNA is the instability of the nucleated blood cells in the urine (i.e. white blood cells) after collection (which instability may be increase as compared to a blood sample). Without steps to stabilize the sample, nucleated blood cells break down post blood draw, resulting in an increase in genomic DNA (gDNA). The increased gDNA serves to dilute the mutation derived DNA (the cell-free nucleic acid being sought) making it much more difficult to detect the actionable mutations and requiring that the techniques be more sensitive than those used for mutation detection performed w/ tissue analysis.

The stabilizing/preserving agent may effectively stabilize/preserve the nucleated blood cells in the urine sample. The stabilizing/preserving agent may prevent cell lysis/breakage that can occur during urine sample handling/storage and or processing. Stabilizing/preserving agents that may be used include, but are not limited to diazolidinyl urea (DU), dimethylol urea, 2-bromo-2-nitropropane-1,3-diol, 5-hydroxymethoxymethyl-1-aza-3,7-dioxabicyclo (3.3.0)octane and 5-hydroxymethyl-1-aza-3,7-dioxabicyclo (3.3.0)octane and 5-hydroxypoly [methyleneoxy]methyl-1-aza-3,7-dioxabicyclo (3.3.0)octane, bicyclic oxazolidines (e.g. Nuosept 95), DMDM hydantoin, imidazolidinyl urea (IDU), sodium hydroxymethylglycinate, hexamethylenetetramine chloroallyl chloride (Quaternium-15), biocides (such as Bioban, Preventol and Grotan), a water-soluble zinc salt or any combination thereof.

Effective stabilization also requires quenching substantially all available free formaldehyde that may be present from stabilizing/preserving agents which release formaldehyde. Free formaldehyde compromises or damages the integrity of the native DNA. If not quenched it will compromise or destroy the structural integrity of the actionable mutations in the cell free DNA and or ctDNA. Furthermore, the quenching of formaldehyde is even more important with regard to urine. As compared to a blood sample, a urine sample contains very few biological components with which the formaldehyde can react with. As a result any remaining free formaldehyde present in the sample will be able to cause damage to target nucleic acids. As a result, whereas blood samples only require minimal quenching of the free formaldehyde, urine samples require that all free formaldehyde be sufficiently quenched.

The formaldehyde quenching agent quenches free formaldehyde that will in fact compromise or damage the integrity of the native DNA. Formaldehyde quenching agents that may be used include, but are not limited to glycine, Tris (hydroxymethyl)aminomethane (TRIS), urea, allantoin, sulfites or any combination thereof.

Stabilization of cell-free DNA in urine further requires blocking of enzymatic active (i.e. DNase activity) in fresh urine to prevent the enzymatic activity that will rapidly hydrolyze nucleic acids. If not effectively blocked, the nucleic acid concentration will decrease quickly as a result of the enzymatic activity that will function to destroy the physical and structural integrity of the nucleic acids. Such enzymatic activity is higher than that found in typical blood samples, but an unexpectedly large increase (at least five times that used in blood stabilization) of nuclease inhibitor is required to compensate.

The nuclease inhibitor inhibits nuclease activity in urine. Nuclease inhibitors that may be used include, but are not limited to ethylene glycol tetraacetic acid (EGTA), pepstatin, $K_3EDTA$, phosphoramidon, leupeptin, aprotinin, bestatin, proteinase inhibitor E 64 (E-64), 4-(2-Aminoethyl) benzenesulfonyl fluoride hydrochloride (AEBSF) or any combination thereof.

The urine sample preservative composition may comprise imidazolidinyl urea (IDU), diazolidinyl urea (DU,) or a combination thereof, a nuclease inhibitor and a formaldehyde scavenging agent. The urine preservative may also comprise imidazolidinyl urea (IDU), diazolidinyl urea (DU) or a combination thereof, glycine, and $K_3EDTA$. The imidazolidinyl urea (IDU) may be present in a concentration (of the preservative composition post contact with a urine sample) of about 0.5% to about 2.0%. The imidazolidinyl urea (IDU) may be present in a concentration of about 0.20% to about 4.0%. The glycine may be present in a concentration of about 0.01% to about 0.2%. The glycine may be present in a concentration of about 0.01% to about 0.4%. The glycine may be present in a concentration of at least about 0.01%, at least about 0.05%, at least about 0.2%, or even at least about 0.3%. The $K_3EDTA$ may be present in a concentration of about 0.5% to about 2.0%. The $K_3EDTA$ may be present in a concentration of about 0.50% to about 3.6%. The $K_3EDTA$ may be present in a concentration of at least about 0.5%, at least about 1%, or even at least about 2.5%. The ratio of $K_3EDTA$ to imidazolidinyl urea (IDU) may be 5:2. The ratio of $K_3EDTA$ to imidazolidinyl urea (IDU) may be from about 1:3 to about 3:1 (e.g., about 9:10, about 9:5 or even about 9:20). The ratio of $K_3EDTA$ to glycine may be from about 5:1 to about 100:1 (e.g., about 50:1 or even about 9:1). The urine preservative may be present in an amount of about 1 to about 20 percent by volume of the specimen container. The urine preservative may be present in an amount of about 1 to about 20 percent by volume of the specimen container. As compared with a composition for stabilizing blood, the composition presented herein for stabilizing urine may have an increased amount of nuclease inhibitor and/or an increased about of formaldehyde quenching agent.

The urine sample may be diluted 5:1 with the preservative agent. For example, 4 parts urine specimen to 1 part urine preservative reagent. The urine sample may be diluted 20:1 with the preservative agent. For example, 19 parts urine specimen to 1 part urine preservative reagent. The urine sample may be diluted 30:1 with the preservative agent. For example, 29 parts urine specimen to 1 part urine preservative reagent.

The sealed vessel of urine preservative may be a single unit dose. The single unit dose may hold a premeasured amount of preservative. The single unit dose may be used for a preserving a single specimen sample. The single unit dose may be labeled with the amount of preservative in the unit dose. The sealed vessel may be a non-reusable container designed to hold a specific amount of preservative.

The urine preservative may be directly contacted with urine sample or the urine sample may be directly contacted with the urine preservative. The contacting step may take place at the collection site. Preferably the contacting step occurs within two hours of obtaining the specimen.

The shipping temperature of the sealed specimen container may be within a range from about 6° C. to about 37° C. The sealed specimen container may be transported without refrigeration or freezing of the preserved urine sample.

The preserved urine sample may exhibit a stability for at least about 7 days post treatment. The preserved urine sample may preserve the original proportion and integrity of nucleic acids in the preserved urine sample. The preserved urine sample may minimize release of cellular nucleic acids from nucleated cells and stabilize nucleic acids. The preserved urine sample may stabilize cell-free nucleic acids in urine at 6° C., 22° C. and 37° C. for at least 7 days.

The step of analysis may be performed 1, 2, 4, or 7 days after the specimen is obtained. The analysis of the urine sample may include urinalysis testing. The analysis of the urine sample may include amplification and quantification of nucleic acids using PCR. The analysis of the urine sample may include nucleic acid sequencing techniques. The analysis of the urine sample may include isolating nucleic acids from the preserved urine sample and analyzing the isolated nucleic acids to identify a pathological condition.

The urine sample method may be performed in the absence of refrigeration of the preserved sample. The urine sample method may be performed in the absence freezing the preserved sample. The preserved sample may be stored at room temperature for a period of least 7 days.

The preservative composition may be present in an amount of about 1 ml to about 15 ml in the preservative delivery vessel. The preservative composition may be present in an amount of about 5 ml to 10 ml in the preservative delivery vessel. The preservative composition may be present in an amount of about 3 ml to about 5 ml in the preservative delivery vessel.

The preservative delivery vessel may be packaged in a plurality of vial strips of single unit dosages. The plurality of vial strips may be packaged in carton. The plurality of vial strips may be packaged as part of a diagnostic kit. The plurality of vials strips may be detachable. The plurality of vial strips may be separated from each other by tearing along a perforation. The plurality of vial strips may be separated from each other by cutting along a specified marking.

The preservative delivery vessel may be formed by injection molding. The preservative delivery vessel may be an injection molded unit dose vial. The injection molding material may include thermoplastic or thermosetting polymers.

The effect of different urine preservative concentrations on stability of urinary cf DNA was examined and compared to untreated urine samples. Untreated urine samples showed a significant decrease in cell-free DNA concentrations of both oncogene KRAS and housekeeping gene β-actin on day 4 and 7 post specimen collection at room temperature. In contrast, cell-free DNA concentrations remained stable for at least 7 days in urine samples treated 5:1 to 30:1 with urine preservative. Moreover, the preservative reagent also stabilized cell-free DNA in urine at 6° C., 22° C. and 37° C. for up to 7 days, whereas untreated samples showed a significant degradation of cell-free DNA at 22° C. and 37° C.

EXAMPLES

To study the effect of different urine preservative concentrations on the stability of urinary cell-free DNA, treated urine samples are examined and compared to untreated urine samples. The first-voided morning urine samples are diluted 5:1, 20:1 or 30:1 with the preservative reagent and stored at room temperature with untreated urine specimens in parallel. Aliquots are removed at specified time points. Cell-free DNA is purified from urine and quantified by a Droplet Digital PCR (ddPCR) assay.

The first-voided morning urine collected from healthy volunteers is treated with urine preservative and is stored at specified temperatures with untreated samples in parallel. Aliquots of urine (5 mL) are removed from each sample on day 0, 4 and 7, respectively. These aliquots are centrifuged at room temperature at 4000 rpm for 10 minutes. 4 mL of supernatant is carefully removed without disturbing pellets and transferred to a new tube using a pipette followed by cfDNA extraction. Urine cfDNA is purified using the commercially available QIAamp® Circulating Nucleic Acid Kit (QIAGEN®, Santa Clarita, Calif.). For optimal results, the manufacturer's recommended protocol is modified slightly by increasing the duration of the proteinase K treatment from 30 min to 1 hour at 60° C. The PCR is performed using the QX100 Droplet Digital PCR system (Bio-Rad, Hercules, Calif.). The KRAS copy number assay kit is purchased from Applied Biosystems (Foster City, Calif.). Primers and the probe for the ddPCR quantification of human β-actinare purchased from Integrated DNA Technologies (Coralville, Iowa).

Results show urinary cfDNA is stabilized by urine preservative over a wide range of dilution ratio at room temperature. Urine was treated 5:1, 20:1 or 30:1 with the urine preservative disclosed herein and stored at room temperature. On day 0, 4 and 7, cfDNA is isolated from urine samples and quantified by ddPCR. The concentration of KRAS gene decreased significantly in untreated urine on day 4 and 7, whereas it remained stable in all treated urine samples for at least 7 days post specimen collection To study the effect of storage temperature on cell-free DNA concentration, both treated and untreated urine samples were stored at 6° C., 22° C. and 37° C. Similarly, cell-free DNA was extracted at various time points and quantified by ddPCR.

The first-voided morning urine collected from healthy volunteers was treated with urine preservative and stored at specified temperatures with untreated samples in parallel. Aliquots of urine (5 mL) are removed from each sample on day 0, 4 and 7, respectively. These aliquots are centrifuged at room temperature at 4000 rpm for 10 minutes. 4 mL of supernatant was carefully removed without disturbing pellets and transferred to a new tube using a pipette followed by cfDNA extraction. Urine cfDNA is purified using the commercially available QIAamp® Circulating Nucleic Acid Kit (QIAGEN®, Santa Clarita, Calif.). For optimal results, the manufacturer's recommended protocol is modified slightly by increasing the duration of the proteinase K treatment from 30 min to 1 hour at 60° C. The PCR was performed using the QX100 Droplet Digital PCR system (Bio-Rad, Hercules, Calif.). The KRAS copy number assay kitiss purchased from Applied Biosystems (Foster City, Calif.). Primers and the probe for the ddPCR quantification of human β-actin are purchased from Integrated DNA Technologies (Coralville, Iowa).

Results show urinary cfDNA stabilized by urine preservative at various storage temperatures. Urine samples are treated 20:1 with urine preservative and stored at 6° C. or 37° C., respectively. cfDNA is isolated from urine samples at specified time points and quantified by ddPCR. The cfDNA (KRAS) is stabilized in all treated urine samples for at least 7 days at either 6° C. or 37° C. No statistically significant difference in cfDNA concentration is found between stored samples and day 0 samples. Similar results are observed for the house keeping gene β-actin.

Examples 1 and 2 demonstrate the effect of different urine preservative concentrations on stability of urinary cfDNA compared to untreated urine samples. Untreated urine samples show a significant decrease in cfDNA concentrations of both oncogene KRAS and housekeeping gene β-actin on day 4 and 7 post specimen collection at room temperature. In contrast, cfDNA concentrations remained stable for at least 7 days in urine samples treated 5:1 to 30:1 with urine preservative. Moreover, the preservative reagent also stabilized cfDNA in urine at 6° C. or 37° C. for up to 7 days.

In addition, the effect of different reagent formulations on stability of urinary cfDNA is examined and compared to untreated urine samples. The urine samples are diluted with various reagent formulations and stored at room temperature with untreated urine specimens in parallel. Aliquots are removed at specified time points. cfDNA (β-actin) is purified from urine and quantified by a Droplet Digital PCR (ddPCR) assay.

FIG. 1 compares the results of unpreserved urine samples and urine samples treated with a reagent for stabilizing blood including about 300 to about 700 g/L IDU, from about 60 to about 100 g/L K$_3$EDTA, and about 20 to about 60 g/L glycine. Results show the reagent for stabilizing blood does not effectively block urine nuclease activity, resulting in DNA degradation. A decrease in cfDNA is associated with nuclease activity and an increase with genomic DNA (unstable WBC). Results indicate that the reagent for stabilizing blood fails to stabilize cfDNA in urine.

Figure 2:
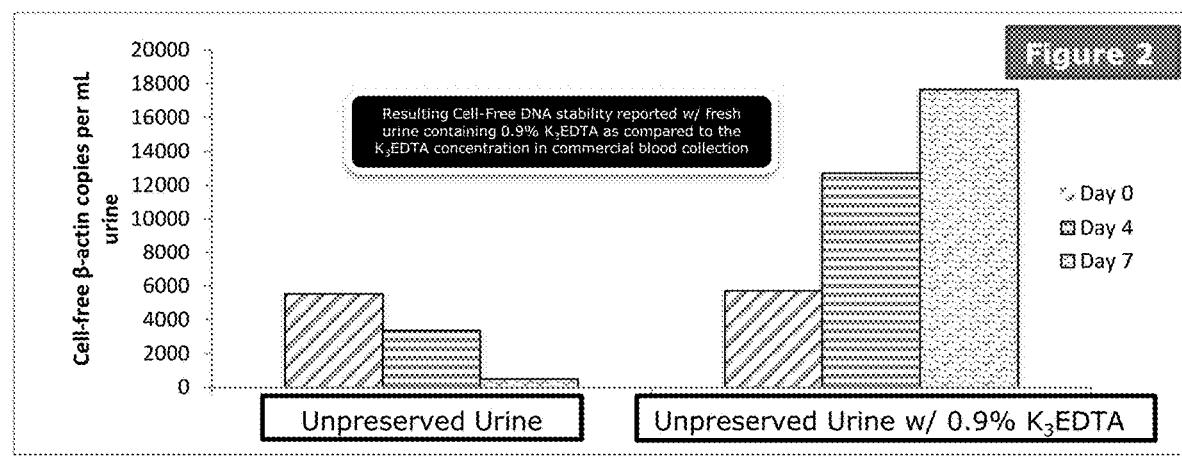
FIG. 2 compares the results of unpreserved urine samples and unpreserved urine samples treated with 0.9% $K_3EDTA$ alone.

FIG. 2 compares the results of unpreserved urine samples and unpreserved urine samples treated with 0.9% $K_3EDTA$. The treated urine samples were treated with a $K_3EDTA$ concentration at around 5× the concentration contained in a commercial $K_3EDTA$ blood collection tube (i.e. 0.17% vs. 0.9%). The nuclease activity was completely blocked by increasing the concentration of the nuclease inhibitor. Results indicate treatment with 0.9% $K_3EDTA$ prevents degradation of the native cell free DNA compliment in urine. However, cellular DNA is released in the absence of an effective nucleated blood cell stabilizer (i.e. WBC degradation).

Urine conditions are markedly different from those of blood. Fresh urine has a higher DNase activity as compared to blood plasma. As seen in FIG. 1, in the absence of nuclease inhibition the native cell free DNA present in fresh urine is grossly unstable, regardless of the presence/concentration of the fixative/stabilizer as commonly used in blood stabilization. FIGS. 1 and 2 illustrate the marked need for a heightened level of nuclease activity inhibition.

Figure 3:
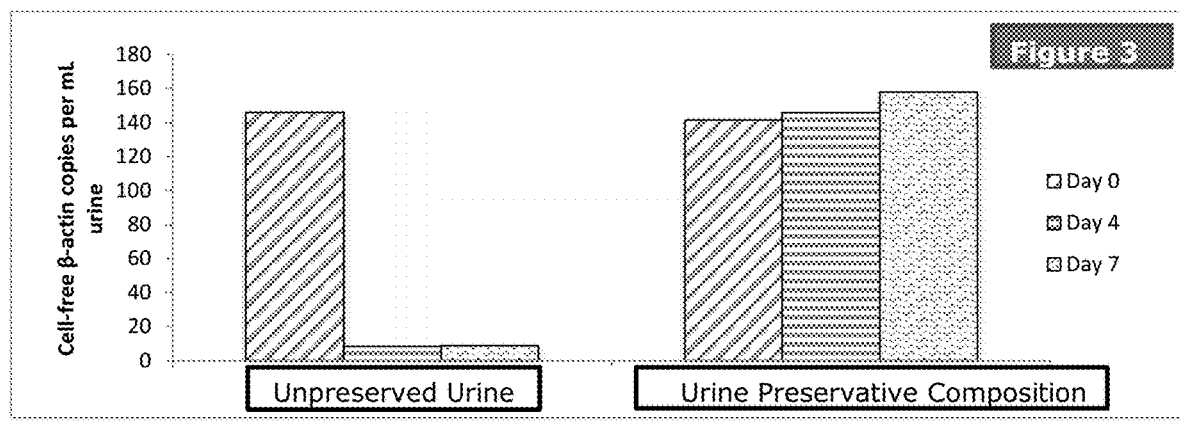
FIG. 3 compares the results of unpreserved urine samples and urine samples treated with the urine preservative composition of the present teachings containing at least 0.9% $K_3EDTA$ in addition to a formaldehyde scavenger and a stabilizing agent.

FIG. 3 compares the results of unpreserved urine samples and urine samples treated with the urine preservative composition disclosed herein. The treated urine samples were treated with a urine preservative composition including about 300 to about 700 g/L imidazolidinyl urea (IDU), about 0.9% $K_3EDTA$ (e.g., from about 100 g/L to about 300 g/L) and at least about 30 g/L glycine. The results indicate that the urine preservative composition stabilizes cfDNA in urine. Therefore, the present teachings provide a preservative reagent that can preserve the original proportion and integrity of cfDNA in urine post specimen collection.

Figure 4:
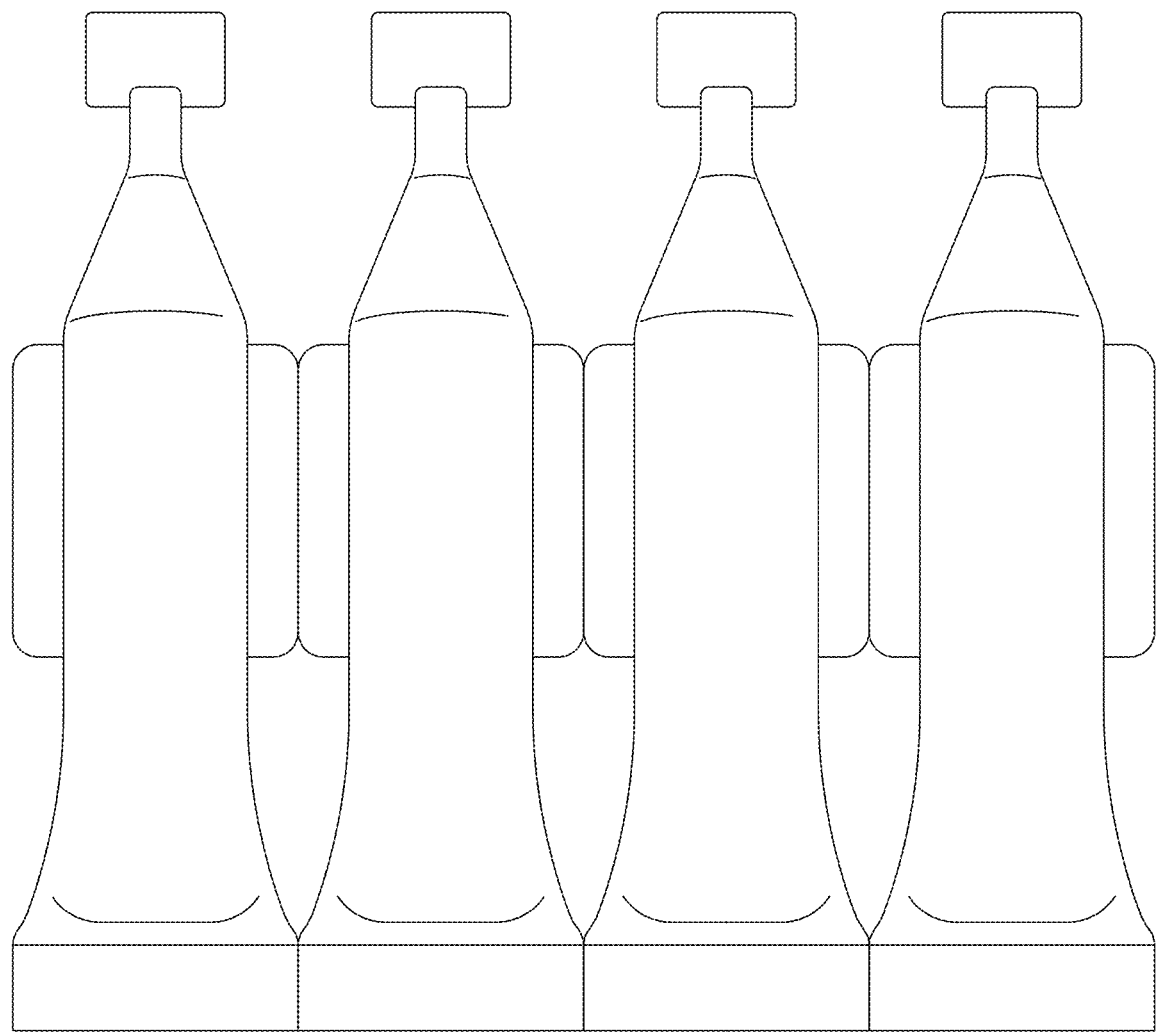
FIG. 4 illustrates a perspective view of the preservative delivery vessel taught herein.

FIG. 4 shows an example container for carrying the urine preservative composition in accordance with the teachings herein. Each individual container can be separately opened and added to a urine sample in accordance with the teachings herein.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The invention claimed is:

1. A urine preservative composition comprising:
 (a) a nuclease inhibitor present in an amount of from about 100 to about 300 g/L of the composition;
 (b) a preservative, wherein the preservative is diazolidinyl urea (DU), dimethylol urea, 2-bromo-2-nitropropane-1,3-diol, 5-hydroxymethoxymethyl-1-aza-3,7-dioxabicyclo (3.3.0)octane and 5-hydroxymethyl-1-aza-3,7-dioxabicyclo (3.3.0)octane and 5-hydroxypoly[methyleneoxy]methyl-1-aza-3,7-dioxabicyclo (3.3.0)octane, a bicyclic oxazolidine, DMDM hydantoin, imidazolidinyl urea (IDU), sodium hydroxymethylqlycinate, hexamethylenetetramine chloroallyl chloride (Quaternium-15), a biocide, a water-soluble zinc salt, or a combination thereof; and
 (c) a formaldehyde quencher, wherein the ratio of nuclease inhibitor to preservative is about 9:10 and the ratio of nuclease inhibitor to formaldehyde quencher is about 9:1.

2. The composition of claim 1, wherein the nuclease inhibitor is ethylene glycol tetraacetic acid (EGTA), pepstatin, $K_3EDTA$, phosphoramidon, leupeptin, aprotinin, bestatin, proteinase inhibitor E 64 (E-64), 4-(2-Aminoethyl) benzenesulfonyl fluoride hydrochloride (AEBSF), or a combination thereof.

3. The composition of claim 1, wherein the formaldehyde quencher is glycine, Tris(hydroxymethyl)aminomethane (TRIS), urea, allantoin, sulfites or a combination thereof.

4. The composition of claim 1, further comprising a urine sample.

5. The composition of claim 4, wherein the urine sample is diluted at a ratio of 4 parts urine sample to 1 part urine preservative composition.

6. The composition of claim 4, wherein the urine sample is diluted at a ratio of 19 parts urine sample to 1 part urine preservative composition.

7. The composition of claim 4, wherein the urine sample is diluted at a ratio of 29 parts urine sample to 1 part urine preservative composition.

8. A method for preserving a urine sample comprising the steps of:
 (a) obtaining the urine sample;
 (b) contacting the urine preservative of claim 1 with the urine sample in a specimen container; and
 (c) sealing the specimen container with the urine sample and the urine preservative contained within it;
 wherein the urine sample, upon being preserved is capable of analysis after a period of at least 168 hours has elapsed.

9. The method of claim 8, wherein the urine preservative comprises:
 imidazolidinyl urea (IDU), diazolidinyl urea (DU) or a combination thereof, and glycine.

10. The method of claim 9, wherein the urine preservative includes $K_3EDTA$ in an amount of at least five times what would be necessary for inhibition of nuclease activity in a blood sample.

11. The method of claim 9, wherein the urine preservative is present in an amount of about 1 to about 20 percent by volume of the specimen container.

12. The method of claim 9, wherein the sealed specimen container is a single unit dose.

13. The method of claim 10, wherein the urine preservative is directly contacted with urine sample or the urine sample is directly contacted with the urine preservative.

14. The method of claim 9, wherein the contacting step is performed within about two hours of obtaining the urine sample.

15. The method of claim 8, wherein the shipping temperature of the sealed specimen container is within a range from about 6° C. to about 37° C.

16. The method of claim 8, wherein the sample exhibits a stability for at least about 7 days post contacting.

17. The method of claim 8, wherein the step of analysis is performed 1, 2, 4, or 7 days after the urine sample is obtained.

18. The method of claim 17, where the analysis of the urine sample includes nucleic acids from the preserved urine sample and analyzing the isolated nucleic acids to identify a pathological characteristic.

19. The method of claim 8, wherein the method is performed in the absence of refrigeration.

20. The method of claim 9, wherein the urine includes one or more of cell free nucleic acids, cellular nucleic acids, DNA, circulating tumor DNA (ctDNA), RNA, microRNA (miRNA), or messenger RNA (mRNA).

21. The method of claim 9, wherein nucleic acid analysis is performed on one or more of a cell free DNA, circulating tumor DNA (ctDNA), cell free RNA, mRNA, or miRNA from within the urine.

22. The method of claim 8, wherein the sealed specimen container contains preservative composition present in an amount of about 1 to about 15 ml.

23. The method of claim 8, wherein the sealed specimen container is packaged in a plurality of vial strips of single unit dosages.

24. The method of claim 8, wherein the sealed specimen container is formed by injection molding.

25. The method of claim 8, wherein, after step (c), the urine sample is processed for isolating a circulating tumor cell, minimal residual disease, a pathogen, or a nucleated cell.

26. The method of claim 25, wherein the nucleated cell is a nucleated blood cell.

27. The composition of claim 4, wherein the nuclease inhibitor is present in a concentration of about 0.5% to about 3.6%.

28. The composition of claim 1, wherein the nuclease inhibitor is $K_3EDTA$ and the preservative is imidazolidinyl urea (IDU).

29. The composition of claim 4, wherein the preservative is present in a concentration of about 0.2% to about 4.0%.

* * * * *

UNITED STATES PATENT AND TRADEMARK OFFICE
CERTIFICATE OF CORRECTION

| | | |
|---|---|---|
| PATENT NO. | : 11,168,351 B2 | Page 1 of 1 |
| APPLICATION NO. | : 15/061557 | |
| DATED | : November 9, 2021 | |
| INVENTOR(S) | : Bradford A. Hunsley et al. | |

It is certified that error appears in the above-identified patent and that said Letters Patent is hereby corrected as shown below:

In the Claims

At Column 10, Lines 5-6, "hydroxymethylqlycinate," should be -- hydroxymethylglycinate, --.

Signed and Sealed this
Seventh Day of June, 2022

Katherine Kelly Vidal
*Director of the United States Patent and Trademark Office*